United States Patent [19]

Lin

[11] Patent Number: 4,487,960
[45] Date of Patent: Dec. 11, 1984

[54] 9-SUBSTITUTED CARBACYCLIN ANALOGS

[75] Inventor: Chiu-Hong Lin, Portage, Mich.

[73] Assignee: The Upjohn Company, Kalamazoo, Mich.

[21] Appl. No.: 369,725

[22] Filed: Apr. 19, 1982

[51] Int. Cl.³ .................... C07C 177/00; C07C 57/26
[52] U.S. Cl. .................................. 560/256; 260/404;
260/404.5; 260/408; 260/410; 260/410.5;
260/410.9 R; 260/413; 260/464; 260/468 D;
549/79; 549/496; 549/501; 560/12; 560/39;
560/45; 560/56; 560/119; 562/427; 562/449;
562/455; 562/466; 562/501; 564/87; 564/88;
564/89; 564/91; 564/96; 564/97; 564/98;
564/99; 564/152; 564/158; 564/159; 564/172;
564/188; 564/428; 564/454; 568/633; 568/655;
568/734; 568/819; 424/305; 424/311; 424/317;
424/320; 424/321; 424/339; 424/343
[58] Field of Search .................... 560/119, 56, 45, 39,
560/12, 256; 562/501, 466, 455, 444, 427;
260/404, 404.5, 408, 410, 410.5, 410.9 R, 413,
465 D, 464; 568/633, 734, 819, 665; 564/172,
188, 158, 159, 132, 87, 88, 89, 91, 96, 97, 98, 99,
428, 454; 549/79, 496, 501

[56] References Cited
U.S. PATENT DOCUMENTS

| 4,180,657 | 12/1979 | Sih ........................... 542/426 |
| 4,192,891 | 3/1980 | Haslanger .................... 424/305 |
| 4,225,508 | 9/1980 | Sih ........................... 260/346.22 |
| 4,238,414 | 12/1980 | Morton, Jr. .................. 564/453 |
| 4,306,075 | 12/1981 | Aristoff ...................... 560/56 |
| 4,306,076 | 12/1981 | Nelson ....................... 560/56 |

FOREIGN PATENT DOCUMENTS

| 2,900,352 | 7/1979 | Fed. Rep. of Germany ...... 560/119 |
| 4024865 | 2/1979 | Japan ......................... 560/119 |
| 4063059 | 5/1979 | Japan ......................... 560/119 |
| 4063060 | 5/1979 | Japan ......................... 560/119 |
| 2012265 | 7/1979 | United Kingdom ............ 560/119 |
| 2,013,661 | 8/1979 | United Kingdom ............ 560/119 |
| 2,017,699 | 10/1979 | United Kingdom ............ 560/119 |

OTHER PUBLICATIONS

Aristoff, P. A., J. Org. Chem., 46 (No. 9), 1981, pp. 1954–1957, "Practical Synthesis of 6a—Carbaprostaglandin I₂".
Barco, A., et al., J. Org. Chem., 45 (No. 23), 1980, pp. 4776–4778, "A New, Elegant Route to a Key Intermediate for the Synthesis of 9(O)—Methanoprostacyclin".
Hayashi, M., et al., Chem. Lett. 1979, pp. 1437–1440, "A Synthesis of 9(O)—Methanoprostacyclin".
Kojima, K., et al., Tetrahedron Lett. 39, 1978, pp. 3743–3746, "Total Synthesis of 9(O)—Methanoprostacyclin and Its Isomers".
Morton, Jr., D. R., et al., J. Org. Chem., 44 (No. 16), 1979, pp. 2880–2887, "Total Synthesis of 6a—Carbaprostaglandin I₂ and Related Isomers".
Nicolaou, K. C., et al., J.C.S. Chem. Comm., 1978, pp. 1067–1068, "Total Synthesis of Carboprostacyclin, a Stable and Biologically Active Analogue of Prostacyclin (PGI₂)".
Shibasaki, M., et al., Chem. Lett. 1979, pp. 1299–1300, "A Stereo and Regiospecific Route to the Synthetic Intermediate for the Synthesis of 9(O)—Methanoprostacyclin".
Shibasaki, M., et al., Tetrahedron Lett. 5, 1979, pp. 433–436, "New Synthetic Routes to 9(O)—Methanoprostacyclin. A Highly Stable and Biologically Potent Analog of Prostacyclin".
Skuballa, W., et al., Angew. Chem., 93 (No. 12), 1981, pp. 1080–1081, "Ein Neuer Weg zu 6a—Carbacyclinen—Synthese eines stabilen, biologisch potenten Prostacyclin—Analogons".
Sugie, A., et al., Tetrahedron Lett., 28, 1979, pp. 2607–2610, "Stereocontrolled Approaches to 9(O)—Methanoprostacyclin".
Yamazaki, M., et al., Chem. Lett. 1981, pp. 1245–1248, "1,2—Carbonyl Transposition of cis—Bicyclo[3.3.0]octan—2—one to Its 3—One Skeleton: Application to Syntheses of dl—Hirsutic Acid and dl—9(O)—Methanoprostacyclin".

Primary Examiner—Robert Gerstl
Attorney, Agent, or Firm—L. Ruth Hattan

[57] ABSTRACT

Novel compounds of the following formula:

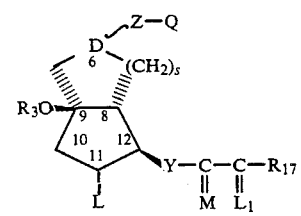

13 Claims, No Drawings

9-SUBSTITUTED CARBACYCLIN ANALOGS

BACKGROUND OF THE INVENTION

The present invention relates to novel compounds which are 9-substituted carbacyclin analogs, to processes for the preparation of said carbacyclin analogs and the use of said analogs as pharmacological agents or as intermediates for the preparation of compounds useful as pharmacological agents. This invention also relates to chemical intermediates for preparing the novel 9-substituted carbacyclin compounds described and claimed herein.

Prostacyclin is an endogenously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "PGI$_2$". For description of prostacyclin and its structural identification, see Johnson, et al, Prostaglandins 12:915 (1976). Carbacyclin, 6a-carba-PGI$_2$, exhibits the structure and carbon atom numbering indicated in formula II when the C-5,6 positions are unsaturated. Likewise, for convenience, carbacyclin is referred to simply as "CBA$_2$".

A stable partially saturated derivative of PGI$_2$ is PGI$_1$ or 5,6-dihydro-PGI$_2$ when the C-5,6 positions are saturated, depicted with carbon atom numbering in formula I when the C-5,6 positions are saturated. The corresponding 5,6-dihydro-CBA$_2$ is CBA$_1$, depicted in formula II when the C-5,6 positions are saturated.

A formula as drawn herein which depicts a prostacyclin-type product or an intermediate useful in the preparation thereof, represents that particular stereoisomer of the prostacyclin-type product which is of the same relative stereochemical configuration as prostacyclin obtained from mammalian tissues or the particular stereoisomer of the intermediate which is useful in preparing the above stereoisomer of the prostacyclin type product. As drawn, formula I corresponds to that of PGI$_2$ endogenously produced in the mammalian species. In particular, refer to the stereochemical configuration at C-8 ($\alpha$), C-9 ($\alpha$), C-11 ($\alpha$) and C-12 ($\beta$) of endogenously produced prostacyclin. The mirror image of the above formula for prostacyclin represents the other enantiomer.

The term "prostacyclin analog" or "carbacyclin analog" represents that stereoisomer of a prostacyclin-type product which is of the same relative stereochemical configuration as prostacyclin obtained from mammalian tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia Nos. 63,059 and 63,060, also abstracted respectively as Derwent Farmdoc CPI Numbers 48154B/26 and 48155B/26. See also British published specification No. 2,012,265 and German Offenlungsschrift No. 2,900,352, abstracted as Derwent Farmdoc CPI Number 54825B/30. See also British published application Nos. 2,017,699 and 2,013,661 and U.S. Pat. No. 4,238,414. The synthesis of carbacyclin and related compounds is also reported in the chemical literature, as follows: Morton, D. R., et al, J. Org. Chem., 44:2880 (1979); Shibasaki, M., et al, Tetrahedron Lett., 433–436 (1979); Kojima, K., et al, Tetrahedron Lett., 3743-3746 (1978); Nicolaou, K. C., et al, J. Chem. Soc., Chemical Communications, 1067–1068 (1978); Sugie, A., et al, Tetrahedron Lett., 2607–2610 (1979); Shibasaki, M., Chem. Lett., 1299–1300 (1979), and Hayashi, M., Chem. Lett., 1437–40 (1979); Aristoff, P. A., J. Org. Chem. 46, 1954–1957 (1981); Yamazaki, M., et al, Chem. Lett., 1245–1248 (1981); and Barco, A., et al, J. Org. Chem. 45, 4776–4778 (1980); and Skuballa, W., et al, Angew. Chem., 93, 1080–1081 (1981). 7-Oxo and 7-hydroxy-CBA$_2$ compounds are apparently disclosed in U.S. Pat. No. 4,192,891. 19-Hydroxy-CBA$_2$ compounds are disclosed in U.S. Ser. No. 054,811, filed July 5, 1979. CBA$_2$ aromatic esters are disclosed in U.S. Pat. No. 4,180,657. 11-Deoxy-$\Delta^{10}$- or $\Delta^{11}$-CBA$_2$ compounds are described in Japanese Kokai No. 77/24,865, published Feb. 24, 1979. Related 9$\beta$-substituted compounds are disclosed in U.S. Pat. Nos. 4,306,075 and 4,306,076.

SUMMARY OF THE INVENTION

The present invention consists of compounds of formula IV wherein D is

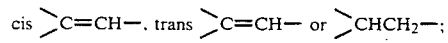

wherein R$_3$ is hydrogen, methyl or acetyl;
wherein Z is
  (1) —CH$_2$—(CH$_2$)$_f$—C(R$_4$)$_2$— wherein each R$_4$ is the same and is hydrogen or fluoro, and f is zero, one, 2 or 3;
  (2) trans-CH$_2$—CH=CH—; or
  (3) —(Ph)—(CH$_2$)$_g$— wherein Ph is 1,2-, 1,3-, or 1,4-phenylene and g is zero, one, 2 or 3;
wherein Q is
  (1) —COOR$_5$, wherein R$_5$ is
    (a) hydrogen,
    (b) (C$_1$-C$_{12}$)alkyl,
    (c) (C$_3$-C$_{10}$)cycloalkyl,
    (d) (C$_7$-C$_{12}$)aralkyl,
    (e) phenyl optionally substituted with one, 2 or 3 chloro or (C$_1$-C$_4$)alkyl,
    (f) phenyl substituted in the para-position with —NHCOR$_6$, —COR$_7$, —OC(O)R$_8$ or —CH=N—NHCONH$_2$, wherein R$_6$ is methyl, phenyl, acetamidophenyl, benzamidophenyl or —NH$_2$; R$_7$ is methyl, phenyl, —NH$_2$, or methoxy; and R$_8$ is phenyl or acetamidophenyl;
    (g) phthalidyl,
    (h) 3-(5,5-dimethyl-1,3,2-dioxaphosphorinan-2-yl)-2-oxopropan-1-yl P-oxide,
    (i) 3-(5,5-di(hydroxymethyl)-1,3,2-dioxaphosphorinan-2-yl)-2-oxopropan-1-yl P-oxide, or
    (j) a pharmacologically acceptable cation;
  (2) —CH$_2$OH;
  (3) —COL$_2$, wherein L$_2$ is
    (a) an amino group of the formula —NR$_9$R$_{10}$ wherein R$_9$ is hydrogen or (C$_1$-C$_{12}$)alkyl and R$_{10}$ is
      (i) hydrogen
      (ii) (C$_1$-C$_{12}$)alkyl
      (iii) (C$_3$-C$_{10}$)cycloalkyl, (iv) $(C_7-C_{12})$aralkyl
(v) phenyl optionally substituted with one, 2 or 3 chloro, $(C_1-C_3)$alkyl, hydroxy, carboxy, $(C_2-C_5)$alkoxycarbonyl, or nitro,
(vi) $(C_2-C_5)$carboxyalkyl,
(vii) $(C_2-C_5)$carbamoylalkyl,
(viii) $(C_2-C_5)$cyanoalkyl,
(ix) $(C_3-C_6)$acetylalkyl,
(x) $(C_7-C_{12})$benzoylalkyl, optionally substituted by one, 2, or 3 chloro, $(C_1-C_3)$alkyl, hydroxy, $(C_1-C_3)$alkoxy, carboxy, $(C_2-C_5)$-alkoxycarbonyl, or nitro,
(xi) pyridyl, optionally substituted by one, 2, or 3 chloro, $(C_1-C_3)$alkyl, or $(C_1-C_3)$alkoxy,
(xii) $(C_6-C_9)$pyridylalkyl optionally substituted by one, 2, or 3 chloro, $(C_1-C_3)$alkyl, hydroxy, or $(C_1-C_3)$alkyl,
(xiii) $(C_1-C_4)$hydroxyalkyl,
(xiv) $(C_1-C_4)$dihydroxyalkyl,
(xv) $(C_1-C_4)$trihydroxyalkyl;
(b) cycloamine selected from the group consisting of pyrolidino, piperidino, morpholino, piperazino, hexamethyleneimino, pyrroline, or 3,4-didehydropiperidinyl optionally substituted by one or 2 $(C_1-C_{12})$alkyl;
(c) carbonylamino of the formula $-NR_{11}COR_{10}$, wherein $R_{11}$ is hydrogen or $(C_1-C_4)$alkyl and $R_{10}$ is other than hydrogen, but otherwise defined as above;
(d) sulfonylamino of the formula $-NR_{11}SO_2R_{10}$, wherein $R_{11}$ and $R_{10}$ are defined in (c);
(4) $-CH_2NL_3L_4$, wherein $L_3$ and $L_4$ are hydrogen or $(C_1-C_4)$alkyl, being the same or different, or the pharmacologically acceptable acid addition salts thereof when Q is $-CH_2NL_3L_4$; or
(5) $-CN$;
wherein s is the integer one or 2;
wherein L is H,H; $\alpha$-$OR_{12}$,$\beta$-H; $\alpha$-H,$\beta$-$OR_{12}$; $\alpha$-$CH_2OR_{12}$,$\beta$-H; $\alpha$-H,$\beta$-$CH_2OR_{12}$ wherein $R_{12}$ is hydrogen or a hydroxyl protective group;
wherein Y is trans $-CH=CH-$, cis-$CH=CH-$, $-CH_2CH_2-$, or $-C\equiv C-$;
wherein M is $\alpha$-$OR_{12}$,$\beta$-$R_{14}$; $\alpha$-$R_{14}$,$\beta$-$OR_{12}$, wherein $R_{12}$ is as defined above, and $R_{14}$ is hydrogen or methyl;
wherein $L_1$ is $\alpha$-$R_{15}$,$\beta$-$R_{16}$; $\alpha$-$R_{16}$,$\beta$-$R_{15}$; or a mixture thereof wherein $R_{15}$ and $R_{16}$ are hydrogen, methyl, or fluoro being the same or different with the proviso that one of $R_{15}$ and $R_{16}$ is fluoro only when the other of $R_{15}$ and $R_{16}$ is hydrogen or fluoro;
wherein $R_{17}$ is
(1) $-C_mH_{2m}CH_3$ wherein m is an integer of from one to 5,
(2) phenoxy optionally substituted by one, 2, or 3 chloro, fluoro, trifluoromethyl, $(C_1-C_3)$alkyl, or $(C_1-C_3)$alkoxy, with the proviso that not more than two substituents are other than alkyl and with the proviso that $R_{17}$ is phenoxy or substituted phenoxy, only when $R_{15}$ and $R_{16}$ are hydrogen or methyl, being the same or different;
(3) phenyl, benzyl, phenylethyl, or phenylpropyl optionally substituted on the aromatic ring by one, 2, or 3 chloro, fluoro, trifluoromethyl $(C_1-C_3)$alkyl, or $(C_1-C_3)$alkoxy, with the proviso that not more than two substituents are other than alkyl,
(4) cis-$CH=CH-CH_2CH_3$,
(5) $-(CH_2)_2-CH(OH)-CH_3$,
(6) $-(CH_2)_3-CH=C(CH_3)_2$, (7)

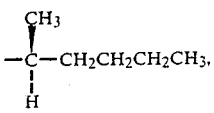

(8)

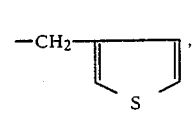

or
(9)

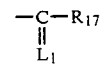

or
wherein

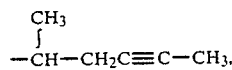

taken together is
(1) $(C_4-C_7)$cycloalkyl optionally substituted by one to 3 $(C_1-C_5)$alkyl,
(2) 3-thienyloxymethyl,
(3)

$$-CH-CH_2C\equiv C-CH_3.$$
$$\phantom{-CH}|$$
$$\phantom{-CH-CH_2C\equiv}CH_3$$

(4) $-C\equiv C-C_qH_{2q}CH_3$ wherein q is an integer of from 2 to 6, or
(5) $-C_pH_{2p}CH=CH_2$ wherein p is an integer of from 3 to 7; and individual optical isomers thereof.

The compounds of Formulas A-2 and C-2 which are useful as intermediates in the preparation of the compounds of Formula IV, are also a part of the present invention. In the various formulas used herein the substituent groups L, Y, M, $L_1$, $R_{17}$, s D, Z, and Q have the same meanings as defined in Formula IV. The group $L_{50}$ is H,H; $\alpha$-OR,$\beta$-H; $\alpha$-H,$\beta$-OR; $\alpha$-$CH_2OR_1$,$\beta$-H; $\alpha$-H,$\beta$-$CH_2OR$ wherein R has the same meaning as $R_{12}$ only R is not hydrogen. The group $M_x$ is $\alpha$-OR,$\beta$-$R_{14}'$, $\alpha$-$R_{14}$,$\beta$-OR wherein R has the same meaning As $R_{12}$ only R is not hydrogen; $R_{14}$ is hydrogen or methyl. The group $R_{13}$ is a hydroxyl protecting group as defined hereinafter. The group $Q_2$ is the same as Q only $Q_2$ is other than $-CH_2OH$. The group $Z_1$ is the same as Z only $Z_1$ is other than $-(Ph)-(CH_2)_g-$.

DETAILED DESCRIPTION OF INVENTION

In naming the novel compounds of the present invention in general the art-recognized system of nomenclature described by N. A. Nelson, J. Med. Chem. 17:911 (1974) for prostaglandins is followed. As a matter of convenience, however, the novel carbacyclin derivatives herein are named as 6a-carba-prostaglandin $I_2$ compounds.

In the formulas herein, broken line attachments to a ring, i.e., (---) indicate substituents in the "alpha" ($\alpha$) configuration, i.e., below the plane of said ring. Heavy solid line attachments to a ring, i.e., (—■) indicate substituents in the "beta" ($\beta$) configuration, i.e., above the plane of said ring. The use of wavy lines ($\sim$) herein will represent attachment of substituents in the alpha or beta configuration or attached in a mixture of alpha and beta configurations. Alternatively wavy lines will represent either an E or Z geometric isomeric configuration or the mixture thereof. Also, solid and dotted lines used together, as for example, in formulas I and II at C-5,6 positions indicates the presence of either a double bond or alternatively a single bond.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel carbacyclin analogs herein.

With regard to the divalent groups described above, i.e., M, L and $L_1$ said divalent groups are defined in terms of an $\alpha$-substituent and a $\beta$-substituent which means that the $\alpha$-substituent of the divalent group is in the alpha configuration with respect to the plane of the C-8 to C-12 cyclopentane ring and the $\beta$-substituent is in the beta configuration with respect to said cyclopentane ring.

The carbon atom content of various hydrocarbon containing groups is indicated by a prefix designating the minimum and maximum number of carbon atoms in the moiety. For example, in defining the moiety $L_2$ in the $-COL_2$ substituent group the definition $(C_1-C_{12})$alkyl means that $L_2$ can be an alkyl group having from one to 12 carbon atoms. Additionally, any moiety so defined includes straight chain or branched chain groups. Thus $(C_1-C_{12})$alkyl as set forth above includes straight or branched chain alkyl groups having from 1 to 12 carbon atoms and as additional illustration, when $L_2$ represents, for example, $(C_2-C_5)$carboxyalkyl, the alkyl moiety thereof contains from 1 to 4 carbon atoms and is a straight chain or a branched chain alkyl group.

Novel compounds wherein Z is $-(Ph)-(CH_2)_g-$ are designated inter-o-, inter-m-, or inter-p-phenylene depending on whether the attachment between C-5 and the $-(CH_2)_g-$ moiety is ortho, meta, or para, respectively. For those compounds wherein g is zero, one or 2, the carbacyclin analogs so described are further characterized as 2,3,4-trinor-, 3,4-dinor-, or 4-nor, since in this event the Q-terminated side chain contains (not including the phenylene) 2, 3, or 4 carbon atoms, respectively, in place of the five carbon atoms contained in $PGI_2$. The missing carbon atom or atoms are considered to be at the C-4 to C-2 positions such that the phenylene is connected to the C-5 and C-1 to C-3 positions. Accordingly these compounds are named as 1,5-, 2,5-, and 3,5-inter-phenylene compounds when g is zero, one, or 2, respectively and when g is 3 the compounds are named as 4,5-inter-phenylene compounds.

The compounds of Formula IV wherein Z is $-CH_2-(CH_2)_f-C(R_4)_2-$ wherein $R_4$ is fluoro are characterized as "2,2-difluoro-" compounds. For those compounds wherein f is zero, 2, or 3, the compounds so described are further characterized as 2-nor, 2a-homo, or 2a,2b-dihomo, since in this event the Q-terminated side chain contains 4, 6, or 7 carbon atoms, respectively, in place of the five carbon atoms contained in $PGI_2$. The missing carbon atom is considered to be at the C-2 position such that the C-1 carbon atom is connected to the C-3 position. The additional carbon atom or atoms are considered as though they were inserted between the C-2 and C-3 positions. Accordingly these additional carbon atoms are referred to as C-2a and C-2b, counting from the C-2 to the C-3 position.

The compounds of Formula IV wherein Z is trans-$CH_2-CH=CH-$ are described as "trans-2,3-didehydro-CBA" compounds.

Those novel compounds where s is 2 are further characterized as 7a-homo-CBA compounds by virtue of the cyclohexyl ring replacing the heterocyclic ring of prostacyclin.

Further, all of the novel compounds of the present invention are substituted at the 9$\beta$-position with a hydroxy group and are named as 9$\beta$-hydroxy compounds, or with a methoxy group and are named 9$\beta$-methoxy compounds, or with an acetoxy group and are named 9$\beta$-acetoxy compounds.

When $R_{14}$ is methyl, the carbacyclin analogs are all named as "15-methyl-" compounds. Further, except for compounds wherein Y is cis-$CH=CH-$, compounds wherein the M moiety contains an hydroxyl in the beta configuration are additionally named as "15-epi-" compounds.

For the compounds wherein Y is cis-$CH=CH-$, then compounds wherein the M moiety contains an hydroxyl in the alpha configuration are named as "15-epi-" compounds. For a description of this convention of nomenclature for identifying C-15 epimers, see U.S. Pat. No. 4,016,184, issued Apr. 5, 1977, particularly columns 24-27 thereof.

The novel carbacyclin analogs herein which contain $-(CH_2)_2-$, cis-$CH=CH-$, or $-C\equiv C-$ as the Y moiety, are accordingly referred to as "13,14-dihydro", "cis-13", or "13,14-didehydro" compounds, respectively.

When $R_{17}$ is straight chained $-C_mH_{2m}-CH_3$, wherein m is an integer of from one to 5, the compounds so described are named as "19,20-dinor", "20-nor", "20-methyl" or "20-ethyl" compounds when m is one, 2, 4 or 5, respectively. When $R_{17}$ is branched chain $-CH_mH_{2m}-CH_3$, then the compounds so described are "17-, 18-, 19-, or 20-alkyl" or "17,17-, 17,18-, -17,19-, 17,20-, 18,18-, 18,19-, 18,20-, 19,19-, or 19,20-dialkyl" compounds when m is 4 or 5 and the unbranched portion of the chain is at least n-butyl, e.g., 17,20-dimethyl" compounds are described when m is 5 (1-methylpentyl).

When $R_{17}$ is phenyl and neither $R_{15}$ nor $R_{16}$ is methyl, the compounds so described are named as "16-phenyl-17,18,19,20-tetranor" compounds. When $R_{17}$ is substituted phenyl, the corresponding compounds are named as "16-(substituted phenyl)-17,18,19,20-tetranor" compounds. When one and only one of $R_{15}$ and $R_{16}$ is methyl or both $R_{15}$ and $R_{16}$ are methyl, then the corresponding compounds wherein $R_{17}$ is as defined in this paragraph are named as "16-phenyl or 16-(substituted phenyl)-18,19,20-trinor" compounds or "16-methyl-16-phenyl- or 16-(substituted phenyl)-18,19,20-trinor" compounds respectively.

When $R_{17}$ is benzyl, the compounds so described are named as "17-phenyl-18,19,20-trinor" compounds. When $R_{17}$ is substituted benzyl, the corresponding compounds are named as "17-(substituted phenyl)-18,19,20-trinor" compounds.

When $R_{17}$ is phenylethyl, the compounds so described are named as "18-phenyl-19,20-dinor" compounds. When $R_{17}$ is substituted phenylethyl, the corresponding compounds are named as "18-(substituted phenyl)-19,20-dinor" compounds.

When $R_{17}$ is phenylpropyl, the compounds so described are named as "19-phenyl-20-nor" compounds. When $R_{17}$ is substituted phenylpropyl the corresponding compounds are named as "19-(substituted phenyl)-20-nor" compounds.

When $R_{17}$ is phenoxy and neither $R_{15}$ nor $R_{16}$ is methyl, the compounds so described are named as "16-phenoxy-17,18,19,20-tetranor" compounds. When $R_{17}$ is substituted phenoxy, the corresponding compounds are named as "16-(substituted phenoxy)-17,18,19,20-tetranor" compounds. When one and only one of $R_{15}$ and $R_{16}$ is methyl or both $R_{15}$ and $R_{16}$ are methyl, then the corresponding compounds wherein $R_{17}$ is as defined in this paragraph are named as "16-phenoxy or 16-(substituted phenoxy)-18,19,20-trinor" compounds or "16-methyl-16-phenoxy- or 16-(substituted phenoxy)18,19,20-trinor" compounds, respectively.

When $R_{17}$ is cis-$CH=CH-CH_2CH_3$, the compounds so described are named as "cis-17,18-didehydro" compounds.

When $R_{17}$ is $-(CH_2)_2-CH(OH)-CH_3$, the compounds so described are named as "19-hydroxy" compounds.

When $R_{17}$ is $-(CH_2)_3-CH=C(CH_3)_2$, the compounds so described are named as "20-isopropylidene" compounds.

When $R_{17}$ is

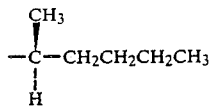

the compounds so described are named as 17(S),20-dimethyl compounds.

When $R_{17}$ is 2-furylmethyl or 3-thienylmethyl, i.e.,

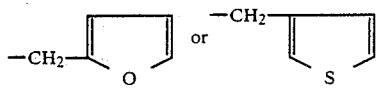

respectively the compounds so described are named as "17-(2-furyl)-18,19,20-trinor" compounds and "17-(3-thienyl)-18,19,20-trinor" compounds respectively.

When

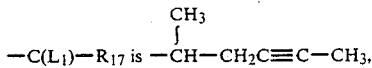

the compounds are named as "16-(R,S)methyl-18,19-tetradehydro" compounds.

When $-C(L_1)-R_{17}$ is optionally substituted cycloalkyl or 3-thienyloxymethyl, the compounds so described are named respectively 15-cycloalkyl-16,17,18,19,20-pentanor compounds and 16-(3-thienyl)oxy-17,18,19,20-tetranor compounds. The term 3-thienyloxymethyl means the moiety having the structure:

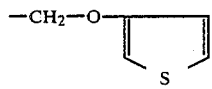

When $-C(L_1)R_{17}$ is $-C\equiv C-C_qH_{2q}CH_3$ wherein q is an integer of from 2 to 6 the compounds so described are named as "16,17-tetradehydro", "16,17-tetradehydro-20-methyl", "16,17-tetradehydro-20-ethyl", "16,17-tetrahydro-20-n-propyl" and "16,17-tetrahydro-20-n-butyl" compounds as the integer as represented by q varies from 2 to 6 respectively.

When $-C(L_1)R_{17}$ is $-C_pH_{2p}CH=CH_2$ wherein p is an integer of from 3 to 7 the compounds so described are named as "19,20-didehydro", "19,20-didehydro-18a,18b-dihomo", "19,20-didehydro-18a,18b,18c-trihomo", "19,20-didehydro-18a,18b,18c,18d-tetrahomo" compounds as the integer represented by p varies from 3 to 7 respectively.

When

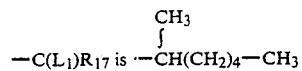

the compounds so described are named as "16(R,S),20-dimethyl" compounds.

When at least one of $R_{15}$ and $R_{16}$ is not hydrogen then (except for the 16-phenoxy or 16-phenyl compounds discussed above) there are described the "16-methyl" (one and only one of $R_{15}$ and $R_{16}$ is methyl), "16,16-dimethyl" ($R_{15}$ and $R_{16}$ are both methyl), "16-fluoro" (one and only one of $R_{15}$ and $R_{16}$ is fluoro), "16,16-difluoro" ($R_{15}$ and $R_{16}$ are both fluoro) compounds. For those compounds wherein $R_{15}$ and $R_{16}$ are different, the carbacyclin analogs so represented contain an asymmetric carbon atom at C-16. Accordingly, two epimeric configurations are possible: "(16S)" and "(16R)". Further, there is described by this invention the C-16 epimeric mixture: "(16RS)".

When Q is $-CH_2OH$, the compounds so described are named as "2-decarboxy-2-hydroxymethyl" compounds.

When Q is $-CH_2NL_3L_4$, the compounds so described are named as "2-decarboxy-2-aminomethyl" or "2-(substituted amino)methyl" compounds.

When Q is $-COL_2$, the novel compounds herein are named as amides. Further, when Q is $-COOR_5$ and $R_5$ is other than hydrogen the novel compounds herein are named as esters and salts.

When Q is CN the novel compounds herein are named as 2-decarboxy-2-cyano compounds.

Examples of phenyl esters substituted in the para position (i.e., Q is $-COOR_5$, $R_5$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is $-COL_2$) include the following:

(1) Amides within the scope of alkylamino groups of the formula $-NR_9R_{10}$ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tert-butylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tertbutylcyclopentylamide, cyclohexylamide, 4-tertbutylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-Nbenzylamide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-chlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutyalmide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)-propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula —NR$_{11}$COR$_{10}$ are methylcarbonylamide, ethylcarbonylamide, phenylcarbonylamide, and benzylcarbonylamide.

(4) Amides within the scope of sulfonylamino of the formula —NR$_{11}$COR$_{10}$ are methylsulfonylamide, ethylsufonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tertbutyl, isopentyl, neopentyl, butyl, pentyl, hexyl, heptyl, octyl, nonyl, decyl, undecyl, dodecyl, isomeric forms thereof.

Examples of $(C_3-C_{10})$cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tertbutylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of $(C_7-C_{12})$aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

Examples of $(C_4-C_7)$cycloalkyl optionally substituted by one to 3 $(C_1-C_5)$alkyl are cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, and cycloheptyl.

Examples of substituted phenoxy, phenyl, phenylmethyl, i.e., benzyl, phenylethyl, or phenylpropyl of the $R_{17}$ moiety are (o-, m-, or p-)tolyl, (o-, m-, or p-)ethylphenyl, 4-ethyl-o-tolyl, 5-ethyl-m-tolyl, (o-, m-, or p-)propylphenyl, 2-propyl-(m- or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(m- or p-)tolyl, 4-fluoro-2,5-xylyl, (2,4-, 2,5-, 2,6-, 3,4-, or 3,5-)difluorophenyl, (o-,m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 4-ethyl-o-tolyloxy, 5-ethyl-m-tolyloxy, (o-, m-, or p-)propylphenoxy, 2-propyl-(m- or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-fluoro-(m- or p-)tolyloxy, 4-fluoro-2,5-xylyloxy, (2,4-, 2,5-, 2,6-, 3,4-, or 3,5-)difluorophenoxy, (o-, m-, or p-)chlorophenoxy, 2-chloro-p-tolyloxy, (3, 4, 5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenyl methyl, 4-ethyl-o-tolylmethyl, 5-ethyl-m-tolylmethyl, (o-, m-, or p-)propylphenylmethyl, 2-propyl-(m- or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(m- or p-)tolylmethyl, 4-fluoro-2,5-xylylmethyl, (2,4-, 2,5-, 2,6-, 3,4-, or 3,5-)difluorophenylmethyl, (o-, m-, or p-)tolylethyl, (o-, m-, or p-)ethylphenylethyl, 4-ethyl-o-tolylethyl, 5-ethyl-m-tolylethyl, (o-, m-, or p-)propylphenylethyl, 2-propyl-(m- or p-)tolylethyl, 4-isopropyl-2,6-xylylethyl, 3-propyl-4-ethylphenylethyl, (2,3,4-, 2,3,5-, 2,3,6-, or 2,4,5-)trimethylphenylethyl, (o-, m-, or p-)fluorophenylethyl, 2-fluoro-(m- or p-)tolylethyl, 4-fluoro-2,5-xylylethyl, (2,4-, 2,5-, 2,6-, 3,4-, or 3,5-)difluorophenylethyl, (o-, m-, or p-)chlorophenylmethyl, 2-chloro-p-tolylmethyl, (3, 4, 5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl, (o-, m-, or p-)chlorophenylpropyl, 2-chloro-p-tolylpropyl, (3, 4, 5, or 6-)chloro-o-tolylpropyl, 4-chloro-2-propylphenylpropyl, 2-isopropyl-4-chlorophenylpropyl, 4-chloro-3,5-xylylpropyl, (2,3-, 2,4-, 2,5-, 2,6-, 3,4-, or 3,5-)dichlorophenylpropyl, 4-chloro-3-fluorophenylpropyl, (3- or 4-)chloro-2-fluorophenylpropyl, (o-, m-, or p-)trifluoromethylphenylpropyl, (o-, m-, or p-)methoxyphenylpropyl, (o-, m-, or p-)ethoxyphenylpropyl, (4- or 5-)chloro-2-methoxyphenylpropyl, and 2,4-dichloro-(4- or 6-)methoxyphenylpropyl.

The group $—C_mH_{2m}CH_3$ wherein m is an integer of from one to 5 which $R_{17}$ may be represents straight or branched alkyl$C_1-C_5$ groups such as named hereinabove.

The terms phthalidyl; 3-(5,5-dimethyl-1,3,2-dioxaphosphorinan-2-yl)-2-oxopropan-1-yl P-oxide; and 3-(5,5-di(hydroxymethyl)-1,3,2-dioxaphosphorinan-2-yl)-2-oxopropan-1-yl P-oxide; which $R_5$ may represent in the $—COOR_5$ group mean the following respective moieties (a), (b) and (c):

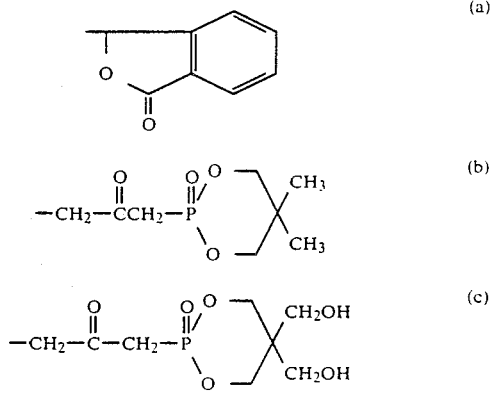

As indicated hereinabove $R_{12}$ is hydrogen or a protecting group. Those protective groups within the scope of $R_{12}$ are any group which replaces a hydroxy hydrogen and is neither attacked by nor is reactive to the reagents used in the transformations used herein as a hydroxy is and which is subsequently replaceable by hydrolysis with hydrogen in the preparation of the carbacyclin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pp. 51–79 (1969). Those blocking groups which have been found useful include:

(a) tetrahydropyranyl;

(b) tetrahydrofuranyl;

(c) a group of the formula —C(OR$_{24}$)(R$_{18}$)—CH(R$_{19}$)(R$_{20}$), wherein R$_{24}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein R$_{18}$ and R$_{19}$ are alkyl of one to 4 carbon atoms, inclusive, phenyl, phenyl substituted with one, 2 or 3 alkyl of one to 4 carbon atoms, inclusive, or when R$_{18}$ and R$_{19}$ are taken together —(CH$_2$)$_a$— or when R$_{18}$ and R$_{19}$ are taken together to form —(CH$_2$)$_b$—O—(CH$_2$)$_c$, wherein a is 3, 4, or 5 and b is one, 2, or 3, and c is one, 2, or 3, with the proviso that b plus c is 2, 3, or 4, with the further proviso that R$_{18}$ and R$_{19}$ may be the same or different, and wherein R$_{20}$ is hydrogen or phenyl; and (d) silyl groups according to R$_{21}$, as qualified hereinafter.

When the protective group R$_{12}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the R$_{12}$ protective group is tetrahydrofuranyl, 2,3-dihydrofuran is used, as described in the preceding paragraph, in place of the 2,3-dihydropyran.

When the R$_{12}$ protective group is of the formula —C(OR$_{24}$)(R$_{18}$)—CH(R$_{19}$)(R$_{20}$), wherein R$_{24}$, R$_{18}$, R$_{19}$, and R$_{20}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

R$_{21}$ is a silyl protective group of the formula —Si(G$_1$)$_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of —Si(G$_1$)$_3$ include trimethylsilyl, dimethylphenylsilyl, triphenylsilyl, t-butyldimethylsilyl, or methylphenylbenzylsilyl. With regard to G$_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to R$_{12}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The protective groups as defined by R$_{12}$ are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

R$_{13}$ is a hydroxyl protective group, as indicated above. As such, R$_{13}$ may be an acyl protective group according to R$_{22}$ as defined below, an acid hydrolyzable protective group according to R$_{12}$ as defined above, or a silyl protective group according to R$_{21}$ as defined above.

Acyl protective groups according to R$_{22}$ include:

(a) benzoyl;

(b) benzoyl substituted with one to 5 alkyl of one to 4 carbon atoms, inclusive, or phenylalkyl of 7 to 12 carbon atoms, inclusive, or nitro, with the proviso that more than two substituents are other than alkyl, and that the total number of carbon atoms in the substituents does not exceed 10 carbon atoms, with the further proviso that the substituents are the same or different;

(c) benzoyl substituted with alkoxycarbonyl of 2 to 5 carbon atoms, inclusive;

(d) naphthoyl;

(e) naphthoyl substituted with one to 9, inclusive, alkyl of one to 4 carbon atoms, inclusive, phenylalkyl of 7 to 10 carbon atoms, inclusive, or nitro, with the proviso that not more than two substituents on either of the fused aromatic rings are other than alkyl and that the total number of carbon atoms in the substituents on either of the fused aromatic rings does not exceed 10 carbon atoms, with the further proviso that the various substituents are the same or different; or (f) alkanoyl of 2 to 12 carbon atoms, inclusive.

In preparing these acyl derivatives of a hydroxy-containing compound herein, methods generally known in the art are employed. Thus, for example, an aromatic acid of the formula R$_{22}$OH, wherein R$_{22}$ is as defined above (e.g., R$_{22}$OH is benzoic acid), is reacted with the hydroxy-containing compound in the presence of a dehydrating agent, e.g. p-toluensulfonyl chloride or dicyclohexylcarbodiimide; or alternatively an anhydride of the aromatic acid of the formula $(R_{22})OH$, e.g., benzoic anhydride, is used.

Preferably, however, the process described in the above paragraph proceeds by use of the appropriate acyl halide, e.g., $R_{22}Hal$, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_{22}$, the following compounds are available as acids $(R_{22}OH)$, $(R_{22})_2O$, or acyl chlorides $(R_{22}Cl)$: benzoyl; substituted benzoyl, e.g., (2-, 3-, or 4-)methylbenzoyl, (2-, 3-, or 4-)ethylbenzoyl, (2-, 3-, or 4-)isopropylbenzoyl, (2-, 3-, or 4-)tertbutylbenzoyl, 2,4-dimethylbenzoyl, 3,5-dimethylbenzoyl, 2-isopropyltoluyl, 2,4,6-trimethylbenzoyl, pentamethylbenzoyl, phenyl (2-, 3-, or 4-)toluyl, (2-, 3-, or 4-)phenethylbenzoyl, (2-, 3-, or 4-)nitrobenzoyl, (2,4, 2,5-, or 2,3-)dinitrobenzoyl, 2,3-dimethyl-2-nitrobenzoyl, 4,5-dimethyl-2-nitrobenzoyl, 2-nitro-6-phenylethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (, 4-, 6-, 7-, or 8-)-methyl-1-naphthoyl, 4-ethyl-2-naphthoyl, and (5- or 8-)nitro-2-naphthoyl and acetyl.

There may be employed, therefore, benzoyl chloride, 4-nitrobenzoyl chloride, 3,5-dinitrobenzoyl chloride, or the like, i.e. $R_{22}Cl$ compounds corresponding to the above $R_{22}$ groups. If the acyl chloride is not available, it is prepared from the corresponding acid and phosphorus pentachloride as is known in the art. It is preferred that the $R_{22}OH$, $(R_{22})_2O$, or $R_{22}Cl$ reactant does not have bulky hindering substituents, e.g. tert-butyl on both of the ring carbon atoms adjacent to the carbonyl attaching site.

The acyl protective groups, according to $R_{22}$, are removed by deacylation. Alkali metal carbonate or hydroxide are employed effectively at ambient temperature for this purpose. For example, potassium carbonate or hydroxide in aqueous methanol at about 25° C. is advantageously employed.

The novel CBA analogs disclosed herein wherein $R_{12}$ is hydrogen produce certain prostacyclin-like pharmacological responses.

Accordingly, the novel formula IV compounds wherein $R_{12}$ is hydrogen are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and additionally the compounds wherein s is one are useful as antithrombotic agents as indicated below.

(a) Platelet Aggregation Inhibition

The compounds of formula IV wherein $R_{12}$ is hydrogen, and s is one are useful whenever it is desired to inhibit platelet aggregation, to reduce the adhesive character of platelets, or to remove or prevent the formation of thrombi in mammals, including man. For example, these compounds are useful in the treatment and prevention of myocardial infracts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2-4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001-1.0 µg per ml of whole blood. These compounds, i.e., the compounds of formula IV wherein $R_{12}$ is hydrogen, and s is one are useful in the treatment of peripheral vascular diseases, in the same manner as described in U.S. Pat. No. 4,103,026.

(b) Gastric Secretion Reduction

Compounds of Formula IV wherein $R_{12}$ is hydrogen are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 µg to about 20 µg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes.

As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

Compounds of Formula IV wherein $R_{12}$ is hydrogen are also useful in reducing the undesirable gastrointestinal effects resulting from systemic administration of anti-inflammatory prostaglandin synthetase inhibitors, and are useful for that purpose by concomitant administration of said compounds of Formula IV and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula IV compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formula IV wherein $R_{12}$ is hydrogen are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use Formula IV compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula IV compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When Q is $-COOR_5$, the novel Formula IV compounds so described are used for the purposes described above in the free acid form, in ester form, or in pharmacologically acceptable salt form. When the ester form is used, the ester is any of those within the above definition of $R_5$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula IV for the purposes described above are those with pharmacologically acceptable metal cations, ammonia, amine cations, or quaternary ammonium cations. Illustrative pharmacological acceptable cations which $R_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl) aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammoniun, tetraethylammonium, benzyltrimethylammonium, phenyltriethylammonium, and the like.

When Q is $-CH_2NL_3L_4$, the Formula IV compounds so described are used for the purposes described in either free base or pharmacologically acceptable acid addition salt form.

The acid addition salts of the 2-decarboxy-2-aminomethyl- or 2-(substituted aminomethyl)-Formula IV compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula IV with the stoichiometric amount of the acid corresponding to the pharmacologically acceptable acid addition salt.

The compounds of Formula IV wherein $R_{12}$ is a hydroxyl protecting group are useful as intermediates to the compounds of Formula IV wherein $R_{12}$ is hydrogen.

To obtain the optimum combination of biological response specificity, potency, and duration of activity, certain compounds within the scope of this invention are preferred. Preferred compounds of the present invention are the $CBA_2$ analogs, i.e., the compounds of Formula IV wherein the C-5,6 position is unsaturated, and of these compounds those wherein Y is $-CH_2CH_2-$, $-C\equiv C-$ or trans-$CH=CH-$ and/or Q is $-COOR_5$ or $-COL_2$ are preferred especially when $R_5$ is hydrogen, methyl, ethyl, or a pharmacologically acceptable cation such as sodium, and when each of $R_9$ and $R_{10}$ of the $L_2$ substituent moiety is hydrogen. To further characterize the preferred embodiments of the present invention, compounds of Formula IV wherein $R_{17}$ is $-C_mH_{2m}CH_3$, benzyl, phenoxy, 3-thienylmethyl, or phenyl or wherein $-C(L_1)R_{17}$ taken together is cyclohexyl, 3-thienyloxymethyl or 3-ethylcyclobutyl, or $-CH(-CH_3)CH_2C\equiv CCH_3$ are especially preferred. Also compounds wherein $R_{17}$ is $C_mH_{2m}CH_3$ and each of $R_{15}$ and $R_{16}$, which make up the $L_1$ substituent, are fluoro are especially preferred.

Preferred for biological potency are formula IV $CBA_2$ analogs exhibiting the same C-5 isomeric configuration as $CBA_2$ itself. As is apparent from the foregoing as compounds satisfy more of the above preferences, said compounds are more preferred.

The carbacyclin analogs of the present invention as represented by Formula IV are prepared by various procedures which are all generally known in the art. The charts provided herein are useful in illustrating the preparation of the compounds.

As indicated hereinabove the hydroxyl groups at positions C-11 and C-15 of the compounds of the present invention may be protected by various groups generally employed in the art and protection of the hydroxyl functions and is generally desirable or necessary during the preparation of the components. Although any of the various protecting groups described herein may be employed those preferred are tetrahydropyranyl (THP) and tert-butyldimethylsilyl. Particularly, THP is a preferred protecting group during the various reactions required to add the side chains and t-butyldimethylsilyl is a preferred group to employ during separation of the isomers. Of course it may be useful or desirable to utilize protecting groups which may be selectively hydrolyzed. Also, when $R_{17}$ is $-(CH_2)_2CH(OH)-CH_3$ the hydroxyl group at C-19 generally is protected by the same type of groups utilized to protect the C-11 and C-15 hydroxyl groups during the preparation of said compounds and subsequently deprotected by hydrolysis as described herein.

Also, it will be apparent that in the preparation of the compounds the 5(E) and 5(Z) isomers generally may be separated when the C-11 and C-15 hydroxyl groups are either protected or are unprotected. However, it has been found that protection of these hydroxyl groups with, e.g., tert-butyldimethyl silyl often facilitates clean separation of the isomers in high yield. Separation of the 5(E) and 5(Z) isomers is achieved by conventional means, typically column chromatography is employed.

The compounds of Formula IV wherein Z is other than $-(Ph)-(CH_2)_g-$ and D is cis-$CH=CH-$ or trans-$CH=CH-$ are prepared as depicted in Chart A hereof. An enone of Formula A-1 is epoxidized with alkaline hydrogen peroxide then reduced with aluminum amalgam by procedures known in the art, e.g., see G. L. Bundy, et al., J. Am. Chem. Soc. 94, 2122 (1972) to give the corresponding hydroxy substituted compound of Formula A-2 wherein $R_{12}$ is hydrogen. The enones of Formula A-1 are known in the art or readily prepared by procedures known in the art as set forth hereinafter.

In preparing the compounds of Formula A-4 from the compounds of Formula A-2 the 1-position hydroxyl group is first protected by an $R_{12}$ protecting group as defined hereinabove. The hydroxy protected A-2 compounds are treated with the dianion of Formula A-3 by methods known in the art. See, for example, G. W. Moersch, J. Org. Chem. 36, 1149 (1979) and J. Mulzer, et al., Tetrahedron Lett. 2949 (1978) to give compounds of Formula A-4. The dianion compounds are known in the art or are prepared by procedures known in the art. For example, see the illustrative procedure set forth in Example 2 hereof. The hydroxy acids of Formula A-4 are subjected to decarboxylative dehydration using dimethylformamide dineopentyl acetal by generally known procedures, e.g., see A. Eschenmoser, et al., Helv. Chim. Acta. 58 1450 (1975); S. Hara, et al., Tetrahedron Lett. 1545 (1975) and J. Mulzer, et al., Tetrahedron Lett. 2953 (1978) and 1909 (1979) to give compounds of Formula A-5 which are selectively hydrolyzed to remove the $R_{12}$ protecting group at the C-9 position to give compounds of Formula A-6 wherein $R_3$ is hydrogen. The 9$\beta$-hydroxy compounds of Formula A-6 can be used to prepare the corresponding 9$\beta$-methoxy and 9$\beta$-acetoxy compounds. By treating a 9$\beta$-hydroxy compound of Formula A-6 with a base such as a metal hydride and methyl iodide one obtains the corresponding 9$\beta$-methoxy compound of Formula A-6 wherein $R_3$ is methyl. By treating a 9$\beta$-hydroxy compound of Formula A-6 with acetic anhydride using dimethylaminopyridine as a catalyst one obtains the corresponding 9$\beta$-acetoxy compound of Formula A-6 wherein $R_3$ is acetyl. The chemistry employed to prepare the 9$\beta$-methoxy and 9$\beta$-acetoxy compounds from the 9$\beta$-hydroxy derivatives is well known in the art. The compounds of Formula A-6 can be hydrolyzed to remove the various protecting groups at position C-1 and which may be present at positions C-11, C-15 and C-19 to give the compounds of A-7. Or, the $R_{12}$ silyl protecting group in compounds of Formula A-6 can be selectively hydrolyzed, e.g., by fluoride mediated hydrolysis to give compounds corresponding to those of A-6 only wherein $R_{21}$ is replaced by hydrogen. These C-1 deprotected compounds corresponding to Formula A-6 are used to prepare the compounds of Formula A-7 wherein $Q_2$ is the same as Q except it is other than —CH₂OH. The Formula A-6 compounds can be oxidized, e.g., using Jones reagent or platinum oxide/oxygen oxidation (J. Fried and J. C. Sih, Tetrahedron Lett. 1973, 3899), to the corresponding carboxylic acid which in turn can be converted to the esters and amides of Formula A-8 by conventional means. The C-1 position alcohols corresponding to A-6 also can be oxidized to the corresponding carboxaldehyde which upon treatment with a salt of hydroxylamine gives the oxime which is dehydrated to give the nitrile, i.e., the compounds of Formula A-8 wherein $Q^2$ is CN. These conversions are all carried out by procedures generally known in the art. See, for example, the aforementioned British specifications which describe the synthesis of various carbacyclin compounds, and in particular G. B. No. 2,013,661. The amide also can be reduced to the corresponding amines, i.e., compounds of Formula A-8 wherein $Q^2$ is —CH₂L₃L₄ by using, e.g., lithium aluminum hydride. See U.S. Pat. No. 4,073,808. During the conversion of the C-1 position alcohols corresponding to Formula A-6 to the various other C-1 position derivatives as represented by Formula A-8, the C-11 and C-15 hydroxyl groups and when present the C-19 hydroxyl groups are protected as described herein which groups can ultimately be deprotected by hydrolysis as generally described hereinbefore.

The 5(E) and 5(Z) isomers can be separated using either the compound of Formulas A-6, A-7 or A-8.

The compounds of Formula IV wherein D is cis-CH=CH— or trans-CH=CH— and wherein Z is —(Ph)—(CH₂)$_q$— are prepared as follows reference being made to Chart B. The ketones of Formula A-2 are reduced by conventional means using, for example, a borohydride reducing agent such as sodium, potassium or lithium borohydride, to the corresponding alcohol. The alcohol is converted to a sulfonate derivative, typically a methanesulfonate or toluenesulfonate by treatment with methanesulfonyl chloride or toluenesulfonyl chloride in the presence of a tertiary amine such as triethylamine. The sulfonate derivative is treated with sodium, lithium or potassium thiophenoxide to give the compounds of Formula B-1. The thiophenoxide is preferably prepared by reacting equal molar amounts of thiophenol and a base such as potassium tertiary butoxide just prior to reaction with the sulfonate. The compounds of Formula B-1 are oxidized to the corresponding phenylsulfonate using, e.g., m-chloroperbenzoic acid then treated with a strong base such as n-butyllithium to generate the corresponding anion. The anion is treated with an aldehyde of Formula B-2 and the resulting adduct is treated with acetic anhydride to give compounds of Formula B-3. The compounds of Formula B-3 are treated with sodium amalgam by procedures analogous to those described by P. J. Kocienski, et al., "Scope and Stereochemistry of an Olefin Synthesis from β-Hydroxysulphones", JCS Perkin I, 829–834 (1978) and are selectively hydrolyzed to remove the hydroxyl protecting group at the C-9 position to give the olefins of Formula B-4 wherein $R_3$ is hydrogen. The 9β-hydroxy derivatives of Formula B-4 can be used to prepare the corresponding 9β-methoxy and 9β-acetoxy derivatives to give compounds of Formula B-4 wherein $R_3$ is methyl or acetyl by procedures described hereinabove in connection with the preparation of the compounds of Formula A-6. The compounds of Formula B-4 are used to prepare the products of Formula B-5. The various hydroxyl groups are protected in such a manner to permit selective hydrolysis to give ultimately the deprotected products of Formula B-5. The $R_{21}$ silyl protecting group is conveniently removed via fluoride mediated hydrolysis using, e.g., tetrabutyl ammonium fluoride to give the C-1 position alcohols of Formula B-5 which are utilized to prepare the corresponding carboxylic acids, esters, amides, amines and nitriles of Formula B-5 by the same general procedures as described hereinabove in reference to the preparation of compounds of Formula A-8. The 5(E) and 5(Z) isomers can be separated conveniently using the alcohol corresponding to Formula B-4 and the various C-9, C-11, C-15 and C-19 hydroxyl protecting groups which may be present are removed by mild acid hydrolysis using, e.g., mixtures of water, tetrahydrofuran and acetic acid.

The compounds of Formula B-2 are prepared using known bis-acids of the formula

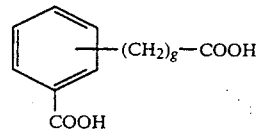

wherein g is zero, one, 2 or 3, which are reduced to the corresponding diol by conventional procedures, e.g., by using lithium aluminum hydride. About equal molar amounts of the diol and a silylating reagent of $R_{21}$ are combined thereby preferentially silylating the alkanol hydroxyl although some di-silylated compound is produced. The mono-silylated compounds of the formula

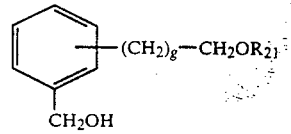

are oxidized to the aldehydes of Formula B-2 by conventional means, e.g., using manganese dioxide. See U.S. Pat. No. 4,306,075.

The compounds of Formula IV may also be prepared as depicted in Chart C hereof. When a compound of C-1, which compounds are known in the art or are readily prepared by means known in the art, is substituted for and treated in the same manner as the compounds of Formula A-1 in Chart A Compounds of Formula C-2 are obtained. When compounds of Formula C-2 are substituted for and treated in the same manner as compounds of Formula A-2 in each of Charts A and B compounds of Formula C-3 are obtained which may be converted to the various C-1 position analogs of Formula C-4 by the general procedures described hereinabove for conversion of compounds of Formula A-6 to A-7. When $R_3$ in Formula C-3 is hydrogen it is preferred that the C-9 hydroxy group is protected by a hydroxy protecting group as defined by $R_{12}$ hereinabove.

Also, the compounds of Formulas C-3 and C-4 can be reduced to the corresponding 5,6-dihydro derivatives of Formula V by known procedures, e.g., as generally described in U.K. application G.B. No. 2,017,699. For example, the reduction may be achieved by a standard hydrogenation in the presence of a catalyst such as palladium on charcoal or platinum dioxide in a lower alkanol such as methanol or ethanol.

The intermediates of Formulas C-3, C-4 and V are utilized in preparing the compounds of Formula IV by procedures which are also useful in preparing compounds of Formula A-1 (Chart A). Initially the intermediates of Formulas C-3, C-4 and V are hydrolyzed to remove the $R_{13}$ protecting group thus giving the primary alcohol derivatives which are oxidized to the corresponding aldehyde by conventional procedures, e.g., under the conditions of a Collins reaction, to give compounds of Formulas C-5, C-6 and VII. To prepare compounds of Formula A-1 one utilizes aldehydes of Formula VI which are obtained by oxidation of the corresponding "C-12 position" substituted alcohol by conventional procedures. The alcohols are known in the art or are readily prepared by procedures known in the art. The aldehydes of Formulas C-5, C-6, VI and VII are then treated as described hereinbelow, wherein for purposes of convenience only the chemical transformations which occur at the "C-12 position" of said compounds are depicted. When $R_3$ in Formulas C-5, C-6 and C-7 is hydrogen it is preferred that the C-9 hydroxy group is protected by a hydroxy protecting group as defined by $R_{12}$ hereinabove.

The "C-12" aldehydes are subjected to a Wittig reaction with the anion of an alkyl phosphonate derivative of the formula

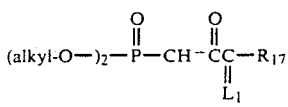

which is obtained by addition of the anion of dialkylmethylphosphonate, i.e.,

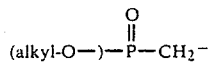

with an ester of the formula

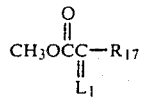

by procedures known in the art, wherein $R_{17}$ and $L_1$ have the same meanings defined in Formula IV, to give the corresponding ketone intermediates wherein W is the group

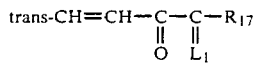

The ketone intermediate is then reduced by dissolving metal hydride reduction to the $\alpha$- or $\beta$-alcohol as defined by M in Formula I to give compounds corresponding to Formulas C-5, C-6, VI and VII only wherein W is the group

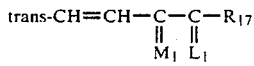

wherein $M_1$ is $\alpha$-OH,$\beta$-H or $\alpha$-H,$\beta$-OH and wherein $L_1$ and $R_{17}$ have the meanings defined in Formula I. The thus obtained trans-vinyl compounds can be hydrogenated to give compounds corresponding to Formulas C-5, C-6, VI and VII only wherein W is the group

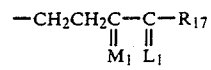

or can be halogenated followed by tetradehydrohalogenation to give the corresponding compounds wherein W is the group

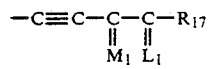

Hydrogenation of the thus obtained acetylene containing compounds with a Lindlar catalyst gives the corresponding cis-vinyl compounds, i.e., compounds corresponding to Formulas C-5, C-6, VI or VII only wherein W is the group

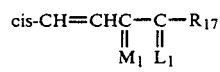

The compounds of Formula A-1 and IV are also prepared by treating a compound of Formula C-5, C-6, VI or VII with a phosphine of the formula (alkyl)$_3$-P=CHCHO under the conditions of a Wittig reaction to give the corresponding compounds wherein W is a trans-vinyl aldehyde group of the formula trans-CH=CHCHO which is reduced to the corresponding trans-vinyl alcohol, i.e., Formula C-5, C-6, VI or VII wherein W is trans-CH=CHCH$_2$OH. The trans-vinyl alcohol can be hydrogenated to give the corresponding compounds wherein W is the group —CH$_2$CH$_2$CH$_2$OH, or the trans-vinyl alcohol can be halogenated then tetradehydrohalogenated to give the corresponding acetylene alcohol, i.e., compounds of Formula C-5, C-6, VI or VII wherein W is the group —C≡CCH$_2$OH. Hydrogenation of the acetylene alcohol with a Lindlar catalyst gives the corresponding cis-vinyl alcohols, i.e., compounds wherein W is the group cis-CH=CHCH$_2$OH.

The thus obtained alcohols, i.e., compounds of Formula C-5, C-6, VI or VII only wherein W is trans-CH=CHCH$_2$OH, —CH$_2$CH$_2$CH$_2$OH, —C≡CH$_2$OH or cis-CH=CHCH$_2$OH are oxidized to the corresponding aldehydes then treated with a Grignard reagent of the formula halo MgCpH$_2$pCH=CH$_2$, wherein halo is a halogen or an alkyl lithium of the formula LiCpH$_2$pCH=CH$_2$, or an acetylide anion of the formula —C≡CCpH$_2$pCH$_3$ or an anion of the formula

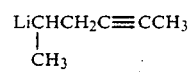

to give the corresponding compounds of Formula wherein W is

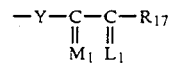

wherein Y, $L_1$ and $R_{17}$ have the meanings defined in Formula I and $M_1$ is a-OH,$\beta$-H or $\alpha$-H,$\beta$-OH. The C-15 hydroxyl group can be protected as required with an $R_{12}$ group as described hereinbefore.

To prepare compounds of Formula A-1 or IV wherein $R_{14}$ of the M substituent group is —$CH_3$ the corresponding C-15 alcohol derivatives are oxidized to the corresponding C-15 ketone then treated with methyl lithium or a methyl Grignard by procedures known in the art.

Removal of protecting groups which may be present at positions C-9 or C-11 is achieved by hydrolysis as generally described hereinabove.

Upon completion of the above-described "C-12 position" transformations with respect to the compounds of Formula VI the resulting lactone derivatives are converted to the compounds of Formula A-1 via lactol and diketone phosphonate derivatives in a manner analogous to that described in U.S. Pat. No. 4,306,075 in reference to Chart A thereof.

A preferred method of preparing the $CBA_1$ compounds of Formula IV wherein Z is trans-$CH_2CH=CH$— is to utilize the appropriate intermediates of Formula C-6 wherein Z is —$CH_2$—$(CH_2)_f$—$C(R_4)_2$— wherein f is one and $R_4$ is hydrogen and wherein $Q^2$ is a carboxylic acid ester, preferably the methyl ester which derivatives are referred to herein as the butanoic acid esters. The butanoic acid ester derivatives are treated with lithium amide base and phenylselenyl chloride to give the corresponding α-phenylselenyl derivatives which are reduced by, e.g., general procedures described in U.K. Application GB No. 2,017,699 to give the 5,6-dihydro intermediates. The 5,6-dihydro intermediates are dehydrophenylselenized by treatment with hydrogen peroxide to give intermediates corresponding to Formula C-6 wherein Z is —$CH_2CH=CH_2$, $Q^2$ is a carboxylic acid ester and the carbon atoms at positions 5 and 6 are saturated, which intermediates can be converted to the corresponding derivatives wherein the terminal C-1 position corresponds to Q as defined herein by the general procedures described hereinabove in connection with the preparation of compounds of Formula B-5 in Chart B. These 5,6-dihydro intermediates are then converted to the $CBA_1$ compounds of Formula IV wherein Z is —$CH_2CH=CH$— by treatment in a manner analogous to that described hereinabove in connection with the conversion of Formula C-6 to $CBA_2$ compounds of Formula IV.

When the alkyl ester has been obtained and an acid is desired, saponification procedures, as known in the art for PGF-type compounds are employed.

When an acid has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield and purity of product.

With regard to the preparation of the phenyl, particularly p-substituted phenyl esters disclosed herein (i.e., Q is —$COOR_5$ and $R_5$ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift No. 2,535,693, and Derwent Farmdoc No. 16828X.

The phthalidyl esters are obtained by treating the corresponding acid with a phthalidyl halide such as the bromide in, e.g., dimethylformamide in the presence of an amine base. The phosphoranyl esters are obtained by treating the corresponding acid with a 1-halo derivative, e.g., the 1-chloro derivative of 3-(5,5-di(hydroxymethyl)-1,3,2-dioxaphosphorinan-2-yl)-2-oxopropan-1-yl P-oxide and 3-(5,5-dimethyl-1,3,2-dioxaphosphorinan-2-yl)-2-oxopropan-1-yl P-oxide in, e.g., acetonitrile in the presence of an organic amine.

Carboxyamides (Q is —$COL_2$) are prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the acids are prepared is, first, by transformation of such free acids to corresponding mixed acid anhydrides. By this procedure, the carbacyclin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at $-10°$ C. to $20°$ C.

Thereafter, the mixed anhydride is converted to the corresponding amido or cycloamido derivatives by reaction with the amine corresponding to the amide to be prepared. In the case where the simple amide ($-NH_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete.

Thereafter, the novel amido or cycloamido derivative is recovered from the reaction mixture by conventional techniques.

The carbonylamido and sulfonylamido derivative of the presently disclosed carbacyclin compounds are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure carbacyclin sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temparatures at or about $0°$ C. are employed.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation if inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

EXAMPLE 1

(a)

3-Oxo-7α-tetrahydropyran-2-yloxy-6β[(3'S)-tetrahydropyran-2-yloxy-trans-1'-octenyl]-bicyclo-[3.3.0]oct-1-ene-1,2-oxide A solution of 11.69 g (27.0 mmol) of 3-oxo-7α-tetrahydropyran-2-yloxy-6β[(3'S)-3'-tetrahydropyran-2-yloxy-trans-1'-octenyl]-bicyclo-[3.3.0]oct-1-ene, 20 ml of 30% hydrogen peroxide, and 200 ml of isopropanol was cooled to $-40°$ C. This solution was treated dropwise with 25 ml of 3N lithium hydroxide reagent over 10 minutes and the resulting solution was allowed to warm between $-25°$ to $20°$ C. and stirred for 2 hours. An additional 2 ml of 3N lithium hydroxide reagent was added followed by 5 ml of 30% hydrogen peroxide. While maintaining the temperature between $-25°$ to $-20°$ C. the reaction was stirred in additional 2 hours. The reaction mixture was neutralized to pH 7 by the addition of 10% sodium bisulfate. Iso-propanol was removed under reduced pressure and the concentrate was diluted with water and ethyl acetate. Solid sodium bisulfite was added (until bubbling ceased) to remove excess hydrogenperoxide (addition of ice was necessary to moderate the exothermic reaction). The mixture was extracted with ethyl acetate (500 ml) and the organic phase was washed with brine, dried over anhydrous magnesium sulfate, filtered, and concentrated in vacuo to give the crude product as a yellow oil. This material was chromatographed on 1 kg silica gel-60 (63–200μ), eluting with hexane-acetone (8:1) to give the title compound.

NMR (CDCl$_3$, TMS) δ: 5.92–5.15 (m, 2H, —CH═CH—), 4.67 (broad s, 2H, —O—CH—O—), 3.33–2.12 (m, 6H, —CH$_2$—O—, —CH—O—), and 3.26 (s, 1H,

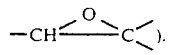

Infrared (film) νmax: 2930, 2860, 1740, 1435, 1200, 1125, 1070, 1020, 970, 865, and 815 cm$^{-1}$.

TLC (Silica gel GF): Rf 0.44 in hexane-ethyl acetate (2:1).

(b)
5β-Hydroxy-7-oxo-3α-tetrahydropyran-2-yloxy-2β-[(3'S)-3'-tetrahydropyran-2-yloxy-trans-1'-octenyl]-bicyclo-[3.3.0]-octane Twenty grams of aluminum turnings (20 mesh) were washed with 100 ml of ether followed by 100 ml of methanol. A saturated solution of mercuric chloride (100 ml) was added to the washed aluminum, swirled, and decanted when vigorous hydrogen evolution was evident. This amalgam was then washed with methanol (2×100 ml) followed by ether (100 ml). A solution of 3-oxo-7α-tetrahydropyran-2-yloxy-6β[(3'S)-tetrahydropyran-2-yloxy-trans-1'-octenyl]-bicyclo-[3.3.0]-oct-1-ene-1,2-oxide (9.91 g, 22.1 mmol) in 200 ml of ether was added in one portion to the amalgam. Methanol (20 ml) and water (2 ml) were added and the resulting mixture was stirred for 2 hours at room temperature. The mixture was filtered and the residue was washed with ethyl acetate. The combined filtrates were concentrated in vacuo to give 10.04 g of crude product as a colorless oil. This material was chromatographed on 1.2 kg of silica gel-60 (63-200μ) eluting with hexane-acetone and concentrated in vacuo to give the title compound.

NMR (CDCl$_3$, TMS) δ: 5.90-5.11 (m, 2H, —CH═CH—), 4.62 (broad S, 2H, —O—CH—O—), 4.37-3.25 (m, 6H, —CH—O—, —CH$_2$—O—), 2.52 (s, 2H, —C—CH$_2$—CO—).

Infrared: νmax (film): 3430, 2930, 2860, 1740, 1465, 1450, 1435, 1385, 1350, 1260, 1195, 1100, 1070, 1015, 970, 905, 865, and 815 cm$^{-1}$.

TLC (Silica gel GF): Rf 0.41 in hexane-acetone (2:1).

(c) 5(E and Z)-2-Decarboxy-2-(t-butyldimethylsilyloxy)methyl-9β-hydroxy-6a-carba-prostaglandin I$_2$, 11,15-bis-(tetrahydropyranyl ether)

(1) A round-bottomed flask equipped with a magnetic stirring bar was charged with 11.0 g (24.4 mmol) of [1'-octenyl]-bicyclo-[3.3.0]-octane and 48.8 ml of 1,1,1,3,3,3-hexamethyldisilazane-trimethylchlorosilane-pyridine (6:3:10) at room temperature under a nitrogen atmosphere. The mixture was stirred at room temperature for 10 minutes and the excess reagent was removed by blowing with nitrogen stream. The concentrate (including a white ppt) was diluted with toluene and the mixture was filtered through a layer of Celite. The filtrate was concentrated in vacuo to give a light yellow oil.

(2) A 3-neck, round-bottomed flask equipped with a magnetic stirring bar, a dropping funnel and a gas inlet tube was dried and flushed with nitrogen. The flask was charged with 8.2 g (80.5 mmol) of diisopropylamine and 183 ml of tetrahydrofuran (THF). The solution was cooled to 0°-5° C. and 47.2 ml (73.2 mmol) n-butyllithium in hexane (1.55M) was added dropwise over 5 minutes via dropping funnel. To this mixture a solution of 9.0 g (36.6 mmol) 6-(dimethyl-t-butylsilyloxy)-hexanoic acid in 61 ml of THF was added over 5 minutes. After stirring an additional 10 minutes, the ice-water bath was removed and the mixture was stirred at room temperature. The solution was cooled again to 0°-5° C. and the yellow oil obtained in step (1) dissolved in 61 ml of THF was added over 5 minutes. The ice-water bath was again removed and the solution was stirred at room temperature for 2 hours. The mixture was quenched with saturated ammonium chloride and THF was removed under reduced pressure. The concentrate was carefully acidified with cold 10% sodium bisulfate and extracted with ether (2×1 liter). The ether layer was washed with water (×4) and brine. After drying over anhydrous magnesium sulfate, the solution was filtered through a layer of Celite and the filtrate was concentrated in vacuo to give a crude adduct as an oil, Rf 0.08-0.33 in hexane-ethyl acetate (5:1).

(3) The crude oil obtained in step (2) was dissolved in a solution of 28.2 g (122.0 mmol) of dimethylformamide-dineopentylacetal (DMF-DNPA) and 183 ml of chloroform. The flask was equipped with a magnetic stirring bar, a reflux condenser and a nitrogen inlet tube. The solution was stirred at room temperature overnight (16 hours) and at 65° C. for 8 hours under a nitrogen atmosphere. Chloroform was then removed under reduced pressure and the concentrate was extracted with ether (1 liter). The ether layer was washed with water, cold 10% sodium bisulfate, 1N sodium hydroxide, brine, and dried over anhydrous magnesium sulfate. Activated charcoal was added to decolorize the deep brown color. Filtration and concentration in vacuo gave a brown oil, Rf=0.78 in hexane-ethyl acetate (2:1).

(4) The oil obtained in step (3) was then dissolved in a mixture containing 6.7 g (48.8 mmol) of potassium carbonate and 488 ml of methanol-water (9:1). The mixture was stirred at room temperature for 18 hours. TLC analysis showed the reaction to be completed. Methanol was removed under reduced pressure and the concentrate was extracted with ether (1 liter). The ether layer was washed with water, brine, and dried over anhydrous magnesium sulfate. Filtration and concentration gave a brown oil. HPLC, using 2×324 g silica gel-60 (40-63μ, E. Merck), packed in two Michel-Miller columns, eluting with hexaneacetone, afforded the title compound as a pale yellow oil.

NMR (CDCL$_3$, TMS) δ: 5.86-5.13 (m, 3H, —CH═CH—), 4.80-4.60 (m, 2H, —O—CH—O—), 4.32-3.34 (m and t, 8H, —CH—O—, —CH$_2$—O—), 0.88 (s and t, 12H, —Si—t—Bu, and CH$_3$).

IR (film) νmax: 3400, 2930, 2850, 2730, 1660, 1630, 1460, 1440, 1380, 1350, 1255, 1200, 1180, 1025, 980, 905, 870, 840, 810, and 780 cm$^{-1}$.

TLC (Silica gel GF): Rf 0.25 in hexane-acetone (3:1).

(d) 5(E and Z)-2-Decarboxy-2-hydroxymethyl-9β-hydroxy-6a-carba-prostaglandin I$_2$ A round-bottomed flask equipped with a magnetic stirring bar was charged with 1.9 g (3.0 mmol) of 5(E and Z)-2-decarboxy-2-(t-butyldimethylsilyloxy)-methyl-9β-hydroxy-6a-carba-prostaglandin I$_2$, 11,15-bis(tetrahydropyranyl ether), 6 ml of 1N HCl, and 24 ml of iso-propano°l. The mixture was stirred at room temperature for 24 hours. The solution was then neutralized with saturated sodium bicarbonate to pH 7 and iso-propanol was removed under reduced pressure. The concentrate was extracted with ethyl acetate (2×1 liter). The organic phase was washed with brine and dried over anhydrous magnesium sulfate. Filtration and concentration afforded a yellow oil. HPLC, using 324 g silica gel-60 (40–63μ, E. Merck), eluting with methylene chloride-acetone-ethanol (10:10:1), and taking 40 ml fractions, gave two major products with very similar polarity. The less polar component contained mostly the E isomer. The more polar component contained mostly the Z isomer. Crystallization of the less polar component from ethyl acetate gave a white solid (m.p. 131°–132° C., 406.2 mg, pure E isomer). The mother liquor of this crystallization was combined with the more polar component and repurified by HPLC using the same condition as described above. Fractions 64–71 (40.0 mg) gave mostly the E isomer, fractions 72–80 (95.5 mg) gave the mixture of E and Z isomers, and fractions 81–112 (311.3 mg) gave pure Z isomer as an oil.

E isomer:

NMR (CD$_3$OD, TMS) δ: 5.82–5.18 (m, 3H, —CH═CH—), 4.20–3.70 (m, 2H, —CH—O—), 3.55 (t, 2H, —CH$_2$O), 2.45 (broad s, 2H, —CH$_2$—C═C—).

IR (film) νmax: 3350, 2950, 2930, 2860, 1640, 1440, 1290, 1070, 1020, 970, and 640 cm$^{-1}$.

TLC (Silica gel GF): Rf 0.35 in methylene chloride-acetone-ethanol (10:20:1).

Z isomer:

NMR and IR were very similar to those of E iosmer.

TLC (Silica gel GF): Rf 0.31 in methylene chloride-acetone-ethanol (10:20:1).

EXAMPLE 2

6-(t-Butyldimethylsilyloxy)hexanoic Acid

A round-bottomed flask equipped with a magnetic stirring bar was charged with 22.8 g (0.2 mol) of ε-caprolactone, 8.8 g (0.22 mol) of sodium hydroxide and 200 ml of methanol-water (4:1). The yellow solution was stirred at room temperature under a nitrogen atmosphere for 24 hours. Methanol-water was removed under reduced pressure. Toluene azeotrope was used to remove water. The resulting solid mass was broken up and ground to a fine powder. This powder was heated with 72.0 g (0.48 mol) of t-butyldimethylchlorosilane, 65.3 g (0.96 mol) of imidazole, and 200 ml of dimethylformamide. The mixture was stirred at room temperature under a nitrogen atmosphere for 16 hours. Water (20 ml) was added to this mixture, stirred for 5 minutes, and was diluted with 800 ml of water. The mixture was extracted with 1 liter of hexane-ether (1:1). The aqueous layer was extracted once more with 1 liter of ether. The combined organic phase was washed with water (×2), brine, and dried over anhydrous magnesium sulfate. Filtration and concentration afforded a light yellow oil. This oil was then stirred in a mixture of 27.6 g (0.2 mol) potassium carbonate and 200 mL of methanol-water (4:1). After 3 hours, methanol was removed under reduced pressure. The concentrate was acidified with cold 10% sodium bisulfate until pH 3–5 and the mixture was extracted ether (2×1 liter). The ether layer was washed with water (×3), brine and dried over anhydrous sodium sulfate. Filtration and concentration afforded the crude product. Column chromatography, using 1 Kg CC-4 silica gel, eluting with Skelly B-EtOAc (10:1), gave a pale yellow oil which solidified in the freezer.

EXAMPLE 3

(5E)-9β-Hydroxy-6a-carba-prostaglandin I$_2$

A 3-neck round-bottomed flask equipped with a magnetic stirring bar was charged with 323.4 mg of platinum oxide and 23.8 ml of water. The brown suspension was stirred under hydrogen atmosphere using hydrogenation apparatus at room temperature for one hour. The catalyst turned black and coagulated. The flask was then purged thoroughly with nitrogen and attached with a reflux condenser and a gas inlet tube. The tip of the tube was placed below the surface of the solution. Nitrogen was bubbled through while the mixture was being stirred. After 10 minutes, nitrogen was replaced by oxygen. To this mixture, 709.2 mg of sodium bicarbonate and 10.6 ml of water was added. This was followed by addition of 300 mg (0.851 mmol) of 5(E)-2-decarboxy-2-methyloxy-9β-hydroxy-6a-carba-prostaglandin I$_2$ in 10.6 ml of acetone. The mixture was heated at 60° C. (bath temperature) while stirring and bubbling of oxygen continued. The mixture was acidifed with 10% sodium bisulfate (to pH 5~6), diluted with about 1 liter of acetone and the mixture was filtered through a layer of Celite. The filtrate was concentrated under reduced pressure. The concentrate was saturated with sodium chloride and extracted with ethyl acetate (1 liter). The organic phase was washed with brine (×4) and dried over anhydrous sodium sulfate. Filtration and concentration gave a crude oil which was purified by HPLC using CC-4 silica gel (52.5 g was packed in a Michel-Miller column). Eluting with methylene chloride-acetone (1:1) and concentrating in vacuo gave the title compound as an oil.

NMR (CD$_3$OD, TMS) δ: 5.72–5.12 (m, 3H, —CH═CH—), 4.24–3.60 (m, 2H, —CH—O—).

Infrared (film) νmax: 1710, 1030, and 970 cm$^{-1}$.

TLC (Silica gel GF): Rf 0.38 in chloroform-methanol-acetic acid (10:1:1).

EXAMPLE 4

(5Z)-9β-Hydroxy-6a-carba-prostaglandin I$_2$

Exactly the same procedure as described in Example 3 was followed. Using 242.5 mg of platinum oxide in 17.8 ml of water, adding 531.9 mg of sodium bicarbonate as well as 225 mg (0.638 mmol) of 5(Z)-2-decarboxy-2-methyloxy-9β-hydroxy-6a-carba-prostaglandin I$_2$ and 15.9 ml acetone-water (1:1). The crude product was purified by HPLC using 52.5 g CC-4 silica gel. Eluting with methylene chloride-acetone (2:1), and concentrating in vacuo gave the title compound as an oil.

NMR (CD$_3$OD, TMS): Identical with that of Example 3 except peaks around δ 2.6–1.7.

Infrared: Identical with that of Example 3.

TLC (Silica gel GF): RF 0.35 in chloroform-methanol-acetic acid (10:1:1).

EXAMPLE 5

5(E and Z)-2-Decarboxy-2-hydroxymethyl-9β-hydroxy-6a-carba-prostaglandin I$_2$, 11,15-bis(tetrahydropyranyl ether)

A round-bottomed flask equipped with a magnetic stirring bar was charged with 381.0 mg (0.6 mmol) of 5(E and Z)-2-decarboxy-2-(t-butyldimethylsilyloxy)-methyl-9β-hydroxy-6a-carba-prostaglandin I$_2$, 11,15-bis-(tetrahydropyranyl ether), 1.6 ml of tetra-n-butylammonium fluoride in THF (0.75M) and 3.2 ml of THF. The mixture was stirred at room temperature under a nitrogen atmosphere for 18 hours. THF was removed under reduced pressure and the concentrate was treated with water and extracted with ether. The organic phase was washed with water, 10% sodium bisulfate, saturated sodium bicarbonate, brine, and dried over anhydrous magnesium sulfate. Filtration and concentration in vacuo gave a light yellow oil. HPLC, using 166 g silica gel (40–63μ), eluting with hexane-acetone (3:1), and taking 15 ml fractions, afforded the following products: The less polar component, Rf 0.43 in hexane-acetone (3:2), was assigned as E isomer and the more polar component, Rf 0.39 in the same solvent, was assigned as Z isomer. In addition there was obtained a mixture of E and Z isomers.

NMR (CDCl$_3$, TMS) (for both E and Z isomers) δ: 5.86–5.08 (m, 3H, —CH=CH—, =CH—), 4.82–4.54 (m, 2H, —O—CH—O—), 4.34–3.28 (m and t, —CH—O—, —CH$_2$—O).

IR (film) (for both E and Z isomers) νmax: 3400, 2930, 2850, 1440, 1350, 1260, 1200, 1180, 1120, 1020, 980, 910, and 810 cm$^{-1}$.

EXAMPLE 6

When in the procedure of Example 1(a) (3'S)-7α-tetrahydropyran-2-yloxy-6β-[3'-tetrahydro-2-yloxyoctanyl]bicyclo[3.3.0]octen-3-one or (3'S)-7α-tetrahydropyran-2-yloxy-6β-[3'-tetrahydro-2-yloxy-1'-octynyl]-bicyclo[3.3.0]octen-3-one is substituted for 3-oxo-(3'S)-7α-tetrahydropyran-2-yloxy-6β-[3'-tetrahydropyran-2-yloxy-trans-1'-octenyl]-bicyclo[3.3.0]oct-1-ene and the general procedure of Example 1(a) and 1(b) is otherwise followed one obtains respectively 5β-hydroxy-7-oxo-3α-tetrahydropyran-2-yloxy-2β[(3'S)-3'-tetrahydropyran-2-yloxy-trans-1'-octanyl]bicyclo[3.3.0]octane and 5β-hydroxy-7-oxo-3α-tetrahydropyran-2-yloxy-2β[(3'S)-3'-tetrahydropyran-2-yloxy-trans-1'-octynyl]-bicyclo[3.3.0]octane, and when each of these compounds so obtained is substituted for 5β-hydroxy-7-oxo-3α-tetrahydropyran-2-yloxy-2β-[(3'S)-3'-tetrahydropyran-2-yloxy-trans-1'-octenyl]bicyclo-[3.3.0]octane in Example 1(c) and the procedure of Example 1(c) and 1(d) is followed one obtains respectively the 5E and 5Z isomers of 2-decarboxy-2-hydroxymethyl-9β-hydroxy-13,14-dihydro-6a-carba-prostaglandin I$_2$ and 2-decarboxy-2-hydroxymethyl-9β-hydroxy-13,14-didehydrota-carba-prostaglandin I$_2$.

EXAMPLE 7

When (5Z)-2-decarboxy-2-hydroxymethyl-9β-hydroxy-13,14-dihydro-6a-carba-prostaglandin I$_2$ or (5Z)-2-decarboxy-2-hydroxymethyl-9β-hydroxy-13,14-didehydro-ta-carba-prostaglandin I$_2$ is substituted for (5E)-2-decarboxy-2-hydroxymethyl-9β-hydroxy-6a-carba-prostaglandin I$_2$ in the procedure of Example 3 the following are obtained:
(5Z)-9β-hydroxy-13,14-dihydro-6a-carba-prostaglandin I$_2$ and
(5Z)-9β-hydroxy-13,14-didehydro-6a-carba-prostaglandin I$_2$.

EXAMPLE 8

5(E and Z)-2-Decarboxy-2-(t-butyldimethylsilyloxy)methyl-9β-methoxy-6a-carba-PGI$_2$, 11,15-bis(tetrahydropyranyl ether)

A two-neck round-bottomed flask equipped with a magnetic stirring bar, a dropping funnel, and a gas inlet tube under a nitrogen atmosphere was charged with 576 mg (12 mmol) of sodium hydride (50% active). The hydride was washed twice with dry hexane and the powder was suspended in 20 ml of DMF. 5(E and Z)-2-Decarboxy-2-(t-butyldimethylsilyloxy)methyl-9β-hydroxy-6a-carba-prostaglandin I$_2$, 11,15-bis-(tetrahydropyranyl ether) (1.9 g, 3 mmol) dissolved in 5 ml of dimethylformamide was added. The resulting mixture was stirred at room temperature for one hour. To this mixture 1.7 g (12 mmol) of methyl iodide dissolved in 5 ml of DMF was added dropwise via dropping funnel over 30 minutes. The mixture was stirred at room temperature for 18 hours. The mixture was quenched with saturated ammonium chloride and extracted with ether. The ether layer was washed with water, 10% sodium bisulfate, saturated sodium bicarbonate, brine, and dried over anhydrous magnesium sulfate. Filtration and concentration gave a brown oil. HPLC, using 324 g of silica gel-60 (40–63μ), eluting with hexane-acetone (20:1), and taking 40 ml fractions, afforded 1.6 g (fr. 16–63, 82%) of the title compound as an oil.

NMR (CDCl$_3$, TMS) δ: 5.8–5.1 (m, 3H, —CH=CH—), 4.80–4.58 (m, 2H, —O—CH—O—), 4.24–3.30 (m and 5, 8H, —CH—O—, —CH$_2$—O—), 3.20, 3.18 (s, 3H, —OCH$_3$).

Infrared (film) νmax: 2930, 2850, 1460, 1440, 1360, 1350, 1260, 1200, 1100, 1020, 975, 900, 870, 840, 820, and 780 cm$^{-1}$.

TLC (Silica gel GF) Rf 0.40 in hexane-acetone (3:1).

EXAMPLE 9

5(E and Z)-2-Decarboxy-2-methyloxy-9β-methoxy-6a-carba-prostaglandin I$_2$

A round-bottomed flask equipped with a magnetic stirring bar was charged with 1.4 g (2.2 mmol) of 5(E and Z)-2-decarboxy-2-(t-butyldimethylsilyloxy)methyl-9β-methoxy-6a-carba-prostaglandin I$_2$, 11,15-bis(tetrahydropyranyl ether), 6.6 ml of 1N HCl, and 26.4 ml of iso-propanol. The mixture was stirred at room temperature for 24 hours. Saturated sodium bicarbonate was added until pH 7 and iso-propanol was removed under reduced pressure. The concentrate was extracted with ethyl acetate. The organic layer was washed with brine and dried over anhydrous magnesium sulfate. Filtration and concentration afforded an oil. HPLC, using two HPLC columns attached in a series (324 g and 166 g silica gel-60, 40–63μ), eluting with methylene chloride-acetone-methanol (20:20:1), and taking 40 ml fractions gave two major products with very similar TLC mobility. Fractions 23–27 (344.0 mg) gave mostly E-isomer and fractions 58–85 (382.5 mg) gave mostly Z-isomer. Repurification of each isomer by the same HPLC condition afforded pure E and Z isomers.

E isomer:
NMR (CDCl$_3$, TMS) δ: 5.68–5.05 (m, 3H, —CH=CH—), 4.20–3.60 (m, 7H, —CH—O—, —CH$_2$O—), 3.22 (s, 3H, —OCH$_3$).

Infrared (film) νmax: 3350, 2960, 2930, 2850, 1640, 1460, 1300, 1260, 1060, and 970 cm$^{-1}$.

TLC (Silica gel GF) Rf 0.42 in methylene chloride-acetone-methanol (10:10:1).

Z isomer:
NMR and IR were similar to those of E isomer.
TLC (Silica gel GF) Rf 0.40 in methylene chloride-acetone-methanol (10:10:1).

EXAMPLE 10

(5Z)-9β-Methoxy-6a-carba-prostaglandin I$_2$

The same procedure as described in Example 3 was followed. Using 363.0 mg of platinum oxide in 26.8 ml of water, adding 795.9 mg of sodium bicarbonate as well as 350.0 mg (0.955 mmol) of (5Z)-2-decarboxy-2-methyloxy-9β-methoxy-6a-carba-prostaglandin I$_2$ and 23.9 ml of acetone-water (1:1). The crude product obtained was then purified by HPLC using CC-4 silica gel, eluting with methylene chloride-acetone (2:1), and taking 30 ml fractions. The fractions homogeneous by TLC were combined and concentrated in vacuo to give 302.0 mg (83.2%) of pure (5Z)-9β-methoxy-6a-carba-prostaglandin I$_2$.

NMR (CDCl$_3$, TMS) δ: 5.75–5.08 (m, 3H, —CH= CH—), 4.2–3.5 (m, 2H, —CH—O—), 3.20 (s, 3H, —OCH$_3$), 2.42 (s, 2H, —CH$_2$—C≡C).

Infrared (film) νmax: 1710, 1060, and 970 cm$^{-1}$.

High Resolution Mass Spectrum (as TMS derivative): Calc'd for C$_3$OH$_{57}$O$_5$Si$_3$ (M$^+$—CH$_3$): 581.3514. Found: 581.3502.

TLC (Silica gel GF) Rf 0.29 in chloroform-methanol-acetic acid (20:1:1).

EXAMPLE 11

5(E and Z)-2-Decarboxy-2-(t-butyldimethylsilyloxy)methyl-9β-acetoxy-6a-carba-prostaglandin I$_2$, 11,15-bis-(tetrahydropyranyl ether)

A round-bottomed flask equipped with a magnetic stirring bar was charged with 1.9 g (3.0 mmol) of 5(E and Z)-2-decarboxy-2-(t-butyldimethylsilyloxy)methyl-9β-hydroxy-6a-carba-prostaglandin I$_2$, 11,15-bis-(tetrahydropyranyl ether), 3.0 ml of acetic anhydride and 3.0 ml of pyridine. To this mixture 76 mg of diethylaminopyridine was added. The solution turned yellow in color. After stirring at room temperature for 2 hours the mixture was cooled to 0°–5° C. and −0.6 ml of water was added. The mixture was stirred for 10 minutes and then extracted with ether. The etherlayer was washed with 10% sodium bisulfate, water, saturated sodium bicarbonate, brine and dried over anhydrous magnesium sulfate. Filtration and concentration gave a yellow oil (2.0 g).

NMR (CDCl$_3$, TMS) showed a singlet at δ2.00 indicating —OCOCH$_3$.

Infrared (film) showed νmax 1740 cm$^{-1}$.

TLC (Silica gel GF) showed Rf 0.5 in hexane-acetone (5:1).

EXAMPLE 12

5(E and Z)-2-Decarboxy-2-methyloxy-9β-acetoxy-6a-carba-prostaglandin I$_2$

A round-bottomed flask equipped with a magnetic stirring bar was charged with 2.0 g (3.0 mmol) of 5(E and Z)-2-decarboxy-2-(t-butyldimethylsilyloxy)methyl-9β-acetoxy-6a-carba-prostaglandin I$_2$, 11,15-bis-(tetrahydropyranyl ether), 9 ml of 1N HCL and 36 ml of iso-propanol. The mixture was stirred at room temperature for 24 hours. Saturated sodium bicarbonate was added until the mixture was about pH 7 and iso-propanol was removed under reduced pressure. The concentrate was saturated with sodium chloride and extracted with ethyl acetate. The organic layer was washed with brine and dried over anhydrous magnesium sulfate. Filtration and concentration gave a light yellow oil. The crude oil was subjected to HPLC, using two silica gel-60 (40–63μ) columns (324 g and 321 g) attached in a series, eluting with ethyl acetate-methanol (20:5:1), and taking 30 ml fractions. Fractions 82–96 (540.4 mg) gave E-isomer and fractions 58–84 (577.0 mg) gave Z-isomer.

E isomer:
NMR (CDCl$_3$, TMS) δ: 5.68–5.04 (m, 3H, —CH= CH—), 4.20 (broad s, 3H, —OH), 4.02–3.60 (m, 2H, —CH—O—), 3.54 (t, 2H, —CH$_2$—O—), 2.00 (s, 3H, —O—CO—CH$_3$).

Infrared (film) νmax 3400, 2940, 2870, 1730, 1440, 1370, 1240, 1070, 1020, 970, and 905 cm$^{-1}$.

TLC (Silica gel GF) Rf 0.35 in ethyl acetate-hexane-methanol (20:5:1).

Z isomer:
NMR and IR were very similar to those of E isomer, Rf 0.33 in the same solvent systems.

EXAMPLE 13

(5E)-9β-Acetoxy-6a-carba-prostaglandin I$_2$

The same procedure as described earlier in Example 3 was followed. Using 380.0 mg of platinum oxide in 28 ml of water, adding 833.3 mg of sodium bicarbonate as well as 394.5 mg (1.0 mmol) of (5E)-2-decarboxy-2-methyloxy-9β-acetoxy-6a-carba-prostaglandin I$_2$ and 25 ml of acetone-water (1:1). The crude product obtained was then purified by HPLC using 52.5 g CC-4 silica gel, eluting with methylene chloride-acetone (2:1), and taking 30 ml fractions. The fractions homogeneous by TLC were combined and concentrated in vacuo to give 280.2 mg (58.5% of pure (5E)-9β-acetoxy-6a-carba-prostaglandin I$_2$ (oil).

NMR (CDCl$_3$, TMS) δ: 5.68–5.04 (m, 3H, —CH= CH—), 5.10 (broad s, 3H, —CO$_2$H, —OH), 4.20–3.70 (m, 2H, —CH—O—), 2.00 (s, 3H, —OCOCH$_3$).

Infrared (film) νmax 3600–2400, 1730, 1710, 1440, 1370, 1240, 1080, 1020, and 970 cm$^{-1}$.

TLC (Silica gel GF) Rf 0.32 in chloroform-methanol-acetic acid (20:1:1).

EXAMPLE 14

(a) 1-Bromo-2-butyne

To a stirred solution of 2-butyne-1-ol (10.0 g, 0.143 mol) in 30 ml of ether at 0° C. is added pyridine (4.84 g, 0.06 mol, 0.43 eq) at once followed by careful dropwise addition of phosphorous tribromide (26.3 g, 0.097 mol, 0.68 eq) over a 30 minute period. An additional 10 ml of ether was added to facilitate stirring and the contents warmed to reflux for 2 hous. The reaction mixture is cooled in ice bath, treated cautiously with 70 ml of ice water and extracted with ether (2×150 ml). The combined ether extracts are washed with saturated brine (2×25 ml), the combined aqueous washings extracted with ether (1×50 ml) and the combined organic extracts dried over anhydrous sodium sulfate. The filtrate is concentrated on a rotary evaporator while keeping the water bath temperature less than 10° C. Twice the contents are diluted with 100 ml of pentane and reconcentrated as before. The heterogenous looking oil is dissolved in 300 ml of pentane, dried over anhydrous magnesium sulfate and reconcentrated as before to obtain 11.0 g (58%) of 1-bromo-2-butyne.

(b) 2-Methyl-4-hexynoic acid

Diisopropylamine (26.0 g, 0. 257 mmol, 3.1 eq) in 130 ml of tetrahydrofuran initially at −50° C. is treated dropwise with n-butyllithium (98.8 ml, 1.6M, 0.158 mol, 1.9 eq) over an 8 minute period while allowing the temperature to rise to −25° C. After 5 minutes longer at −20° C., the reaction mixture is treated dropwise with a mixture of hexamethylphosphoramide (17.8 g, 0.099 mol, 1.2 eq) and propionic acid (6.14 g, 0.083 mol, 1.0 eq) over a 7 minute period while the temperature rises to 0° C. Following addition the reaction mixture is warmed to room temperature and maintained there for 35 minutes. The contents are then cooled to 0° C. in an ice bath, treated dropwise over a 12 minute period with 1-bromo-2-butyne (11.0 g, 0.083 mol, 1.0 eq) in 8 ml of tetrahydrofuran. The temperature, which rises to 16° C. during addition, is allowed to warm to room temperature thereafter where it is maintained for 2 hours. The contents are carefully poured into 300 ml of 10% HCl with stirring (exothermic) followed by 500 ml of etherpentane (1:1). The organic layer is separated and the aqueous phase extracted 2 more times with etherpentane (1:1) giving 1800 ml of total extract volume. The combined extracts are washed with water 2×60 ml) and the combined organic extracts are dried over anhydrous sodium sulfate, magnesium sulfate and concentrated at reduced pressure to provide 11.1 g (over theory) of 2-methyl-4-hexynoic acid which is converted to the methyl ester by treatment with methyl iodide.

(c) 3-Methyl-2-oxo-hept-5-yne phosphonic acid dimethyl ester

A solution of dimethyl methylphosphonate (22.47 g, 181.24 mmol) in 260 ml of tetrahydrofuran is cooled to −78° C. and treated dropwise with n-butyllithium (113 ml, 181.24 mmol), 1.6M in hexane) over a 25-minute period. The mixture is stirred an additional 30 minutes at −78° C., then treated dropwise with 2-methyl-4-hexynoic acid methyl ester (7.25 g, 51.78 mmols) in 65 ml of tetrahydrofuran over a period of 10 minutes. The contents are stirred for another 3 hours at 31 78° C. and then 17 hours at ambient temperature. The reaction mixture is cooled to 8° C., treated with 14 ml of acetic acid, stirred at ambient temperature for 30 minutes, then concentrated in vacuo. The residue is treated with 100 ml of saturated brine and 100 ml of ice water to form a slurry and extracted 3 times with ether (1400 ml total) and once with 250 ml of ethyl acetate-ether (1:1). The combined organic extracts are washed with saturated brine (2×75 ml), the combined aqueous washings extracted with ethyl acetate-ether (1:1, 1×100 ml) and dried over anhydrous sodium sulfate, and concentrated at reduced pressure. Vacuum distillation gives 10.21 g of the title product, m.p. 121°–125° C., 0.15 mmHg.

EXAMPLE 15

5(E and Z)-2-Decarboxy-2-(t-butyldimethylsilyloxymethyl)-9β-hydroxy-13,14,15,16,17,18,19,20-octanor-12β-(benzyloxymethyl)-6a-carba-prostaglandin I₂, 11-tetrahydropyranyl ether When in the procedure of Example 1(a) 6β-[(benzyloxy)methyl]-7α-(tetrahydropyran-2-yloxy)-bicyclo[3.3.0]octen-3-one is substituted for 3-oxo-7α-(tetrahydropyran-2-yloxy)-6β-[(3′S)-3′-tetrahydropyran-2-yloxy-trans-1′-octenyl]-bicyclo[3.3.0]oct-1-ene and the general procedure of Example 1(a) and 1(b) is followed one obtains 6β-(benzyloxymethyl)-7α-(tetrahydropyran-2-yloxy)-1β-(hydroxy)-bicyclo[3.3.0]octan-3-one. When this compound is substituted for 5β-hydroxy-7-oxo-3α-tetrahydropyran-2-yloxy-2β-[(3′S)-3′-tetrahydropyran-2-yloxy-trans-1′-octenyl]bicyclo[3.3.0]octane in Example 1(c) and the procedure of Example 1(c) is followed one obtains the title compound.

EXAMPLE 16

5(E and Z)-2-Decarboxy-2-(t-butyldimethylsilyloxymethyl)-9β-hydroxy-13,14,15,16,17,18,19,20-octanor-12β-hydroxymethyl-6a-carba-prostaglandin I₂, 11-tetrahydropyranyl ether Liquid ammonia (100 ml) is distilled into a solution of 5(E and Z)-2-decarboxy-2-(t-butyldimethylsilyloxymethyl)-9β-hydroxy-13,14,15,16,17,18,19,20-octanor-12β-(benzyloxymethyl)-6a-carba-prostaglandin I₂, 11-tetrahydropyranyl ether (5.4 g, 10 mmol) in 100 ml of tetrahydrofuran and 2.0 ml of t-butyl-alcohol at 3150° C. utilizing a dry ice-acetone trap. The temperature is maintained at about −40° C. while freshly scraped lithium wire (4 inches) is added in small pieces until the mixture is turned blue. After stirring the mixture for 30 minutes solid ammonium chloride is added to quench excess lithium. The disappearance of blue color indicates the stoppage of reaction. A nitrogen stream is swept through the flask to expel the excess ammonia. The solid resdue is treated with 100 ml of saturated ammonium chloride and extracted with ethyl acetate. The organic phase is washed with brine and dried over anhydrous magnesium sulfate. Filtration and concentration in vacuo afford the title compound.

EXAMPLE 17

(a) 5(E and Z)-2-Decarboxy-2-(t-butyldimethylsilyloxymethyl)-9β-hydroxy-13,14,15,16,17,18,19,20-octanor-12β-formyl-6a-carba-prostaglandin I₂, 11-tetrahydropyranyl ether Collins oxidation, known in the art, of 5(E and Z)-2-decarboxy-2-(t-butyldimethylsilyloxymethyl)-9β-hydroxy-13,14,15,16,17,18,19,20-octanor-12β-hydroxymethyl-6a-carba-prostaglandin I₂, 11-tetrahydropyranyl ether, the title compound of Example 16, gives the title compound.

(b) 5(E and Z)-2-Decarboxy-2-(t-butyldimethylsilyloxymethyl)-9β-hydroxy-15-keto-16(R,S)-16-methyl-18,19-tetradehydro-6a-carba-prostaglandin I₂, 11-tetrahydropyranyl ether Thallium ethoxide (634 mg, 2.55 mmol) in 10 ml of benzene at 0° C. in a round-bottomed flask is treated with dimethyl-2-oxo-3-methyl-5-heptynyl phosphonate (613 mg, 2.64 mmol) in 2.5 ml of benzene. After stirring for 50 minutes at 0° to 10° C., the title compound in Example 17(a) (889 mg, 1.96 mmol) in 5 mL of benzene is added at once to mixture at 0° C. After stirring the mixture at room temperature for one hour, the mixture is again cooled to 0° C., quenched with 0.5 ml of acetic acid followed by addition of aqueous potassium iodide to precipitate the thallium as a yellow salt. The contents are diluted with ether, stirred at room temperature and filtered through a pad of Celite. The organic phase is washed with ice water, saturated sodium bicarbonate, brine, and dried over anhydrous magnesium sulfate. Chromatographic purification gives the 17(b) title compound.

(c) 5(E and Z)-2-Decarboxy-2-(t-butyldimethylsilyloxymethyl)-9β-hydroxy-15(R,S)-16-methyl-18,19-tetradehydro-6a-carba-prostaglandin I₂, 11-tetrahydropyranyl ether A round-bottomed flask equipped with a magnetic stirring bar is charged with 0.55 g (1.0 mmol) of the title compound in Example 17(b) and 10 ml of methanol. The solution is cooled to −20° to −15° C. and sodium borohydride (76 mg, 2 mmol) is added. The mixture is stirred for one hour and quenched with saturated ammonium chloride. Methanol is removed under reduced pressure and the residue is extracted with ethyl acetate. The organic phase is washed with brine and dried over anhydrous magnesium sulfate. Chromatographic separation resolves the 15(R) and 15(S) isomers.

EXAMPLE 18

(a) 5(E and Z)-2-Decarboxy-2-hydroxymethyl-9β-hydroxy-16(R,S)-16-methyl-18,19-tetradehydro-6a-carba-prostaglandin I₂

When in the procedure of Example 1(d) 5(E and Z)-2-decarboxy-2-(t-butyldimethylsilyloxymethyl)-9β-hydroxy-16(R,S)-16-methyl-18,19-tetradehydro-6a-carba-prostaglandin I₂, 11-tetrahydropyranyl ether is substituted for 5(E and Z)-2-decarboxy-2-(t-butyldimethylsilyloxymethyl)-9β-hydroxy-6a-carba-prostaglandin I₂, 11,15-bis-(tetrahydropyranyl ether), one obtains the title compound. As in the case of Example 1(d), the (5E) and (5Z) isomers are resolved by the chromatographic separation.

(b) 9β-Hydroxy-16(R,S)-16-methyl-18,19-tetradehydro-6a-carba-prostaglandin I₂

When in the procedure of Example 3 (5Z)-2-decarboxy-2-hydroxymethyl-9β-hydroxy-16(R,S)-16-methyl-18,19-tetradehydro-6a-carba-prostaglandin I₂ is substituted for (5E)-2-decarboxy-2-methyl-oxy-9β-hydroxy-6a-carba-prostaglandin I₂ one obtains the title compound after the chromatographic purification.

EXAMPLE 19

When in the procedure of Example 17(b) each of the following phosphonates is substituted for dimethyl-2-oxo-3-methyl-5-heptynyl phosphonate and the procedures of Examples 17(b); 17(c) and 18 are followed one ultimately obtains the 9β-hydroxy products listed below:

dimethyl-2-oxo-3-phenylpropyl phosphonate;
dimethyl-2-oxo-4-phenylbutyl phosphonate;
dimethyl-2-oxo-3-phenoxypropyl phosphonate;
dimethyl-2-oxo-4-(3-thienyl)butyl phosphonate;
dimethyl-2-cyclohexyl-2-oxoethyl phosphonate;
dimethyl-2-oxo-3-(3-thienyloxy)propyl phosphonate; or
dimethyl-2-oxo-2-(3-ethylcyclobutyl)ethyl phosphonate;

5(E and Z)-2-decarboxy-2-hydroxymethyl-9β-hydroxy-16-phenyl-17,18,19,20-tetranor-6a-carba-prostaglandin I₂;
5(E and Z)-2-decarboxy-2-hydroxymethyl-9β-hydroxy-17-phenyl-18,19,20-trinor-6a-carba-prostaglandin I₂;
5(E and Z)-2-decarboxy-2-hydroxymethyl-9β-hydroxy-16-phenoxy-17,18,19,20-tetranor-6a-carba-prostaglandin I₂;
5(E and Z)-2-decarboxy-2-hydroxymethyl-9β-hydroxy-17-(3-thienyl)-18,19,20-trinor-6a-carba-prostaglandin I₂;
5(E and Z)-2-decarboxy-2-hydroxymethyl-9β-hydroxy-15-cyclohexyl-16,17,18,19,20-pentanor-6a-carba-prostaglandin I₂;
5(E and Z)-2-decarboxy-2-hydroxymethyl-9β-hydroxy-16-(3-thienyloxy)-17,18,19,20-tetranor-6a-carba-prostaglandin I₂;
5(E and Z)-2-decarboxy-2-hydroxymethyl-9β-hydroxy-15-(3-ethylcyclobutyl)-16,17,18,19,20-pentanor-6a-carba-prostaglandin I₂;
5(E and Z)-9β-hydroxy-16-phenyl-17,18,19,20-tetranor-6a-carba-prostaglandin I₂;
5(E and Z)-9β-hydroxy-17-phenyl-18,19,20-trinor-6a-carba-prostaglandin I₂;
5(E and Z)-9β-hydroxy-16-phenoxy-17,18,19,20-tetranor-6a-carba-prostaglandin I₂;
5-(E and Z)-9β-hydroxy-17-(3-thienyl)-18,19,20-trinor-6a-carba-prostaglandin I₂;
5(E and Z)-9β-hydroxy-15-cyclohexyl-16,17,18,19,20-pentanor-6a-carba-prostaglandin I₂;
5(E and Z)-9β-hydroxy-16-(3-thienyl-oxy)-17,18,19,20-tetranor-6a-carba-prostaglandin I₂;
5(E and Z)-9β-hydroxy-15-(3-ethylcyclobutyl)-16,17,18,19,20-pentanor-6a-carba-prostaglandin I₂;

FORMULAS

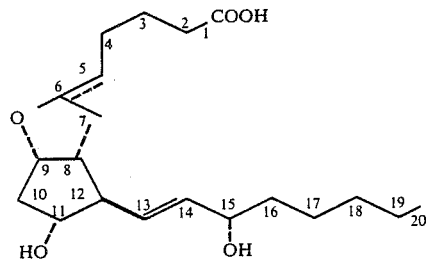

I

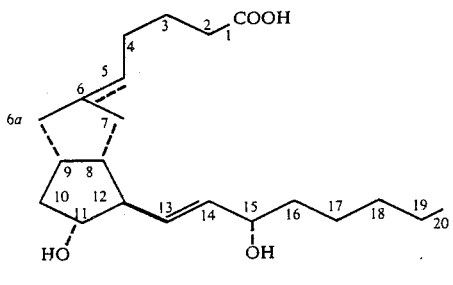

II

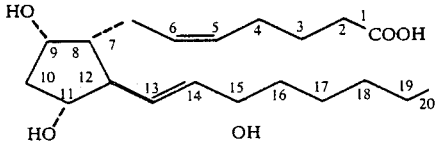

III

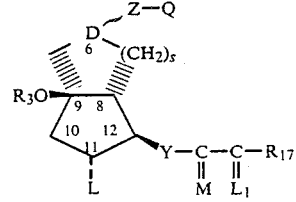

IV

-continued
FORMULAS
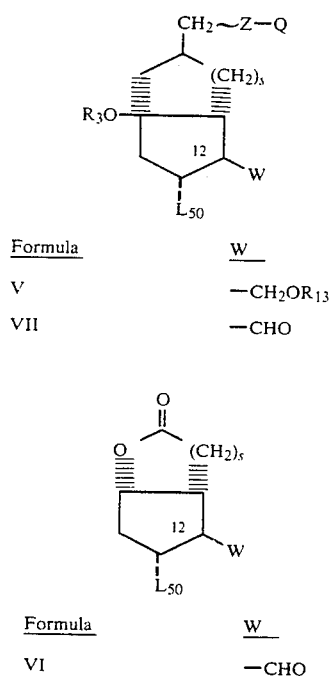
| Formula | W |
|---|---|
| V | —CH$_2$OR$_{13}$ |
| VII | —CHO |
| Formula | W |
|---|---|
| VI | —CHO |
CHART A
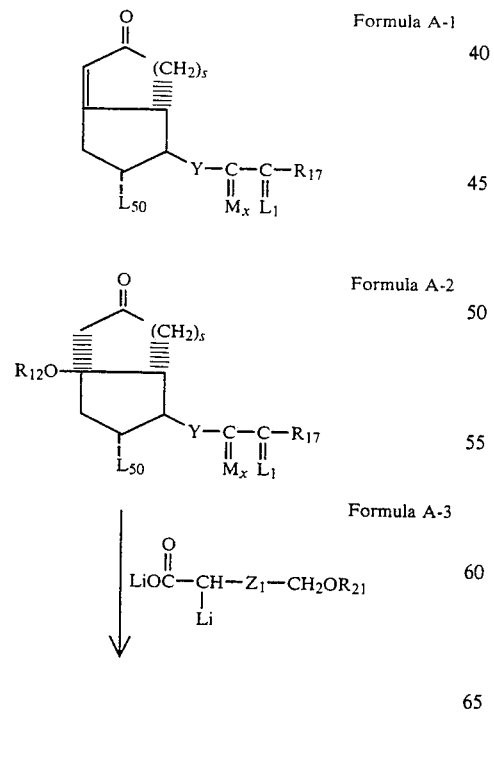
-continued
CHART A
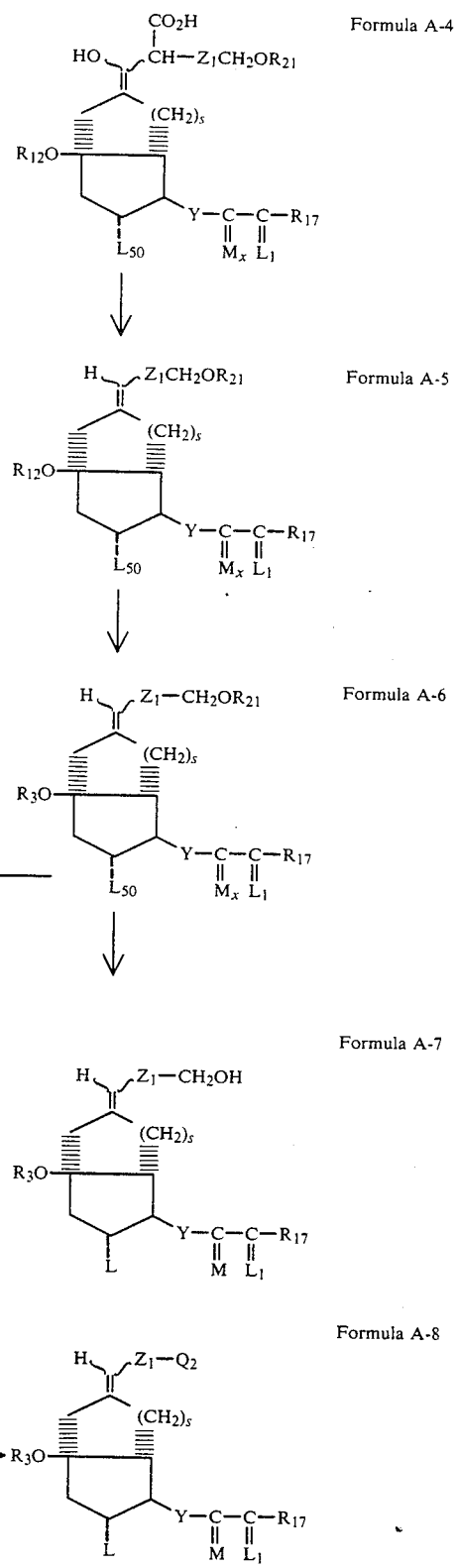

CHART B
Formula A-2 ———→
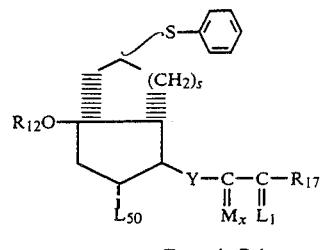
Formula B-1
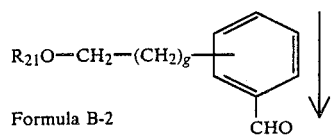
Formula B-2
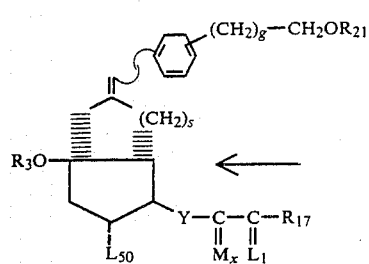
Formula B-4
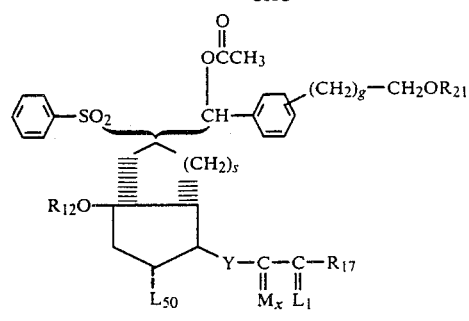
Formula B-3
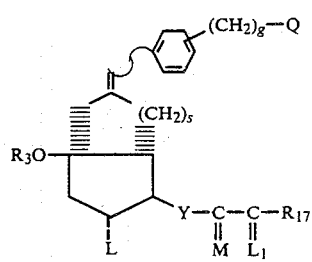
Formula B-5
CHART C
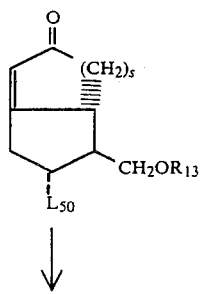
Formula C-1
-continued
CHART C
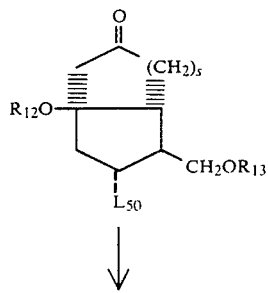
Formula C-2

-continued
CHART C

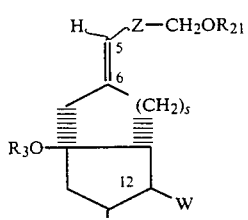

Formula | W
--- | ---
C-3 | —CH$_2$OR$_{13}$
C-5 | —CHO

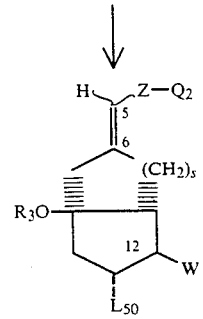

Formula | W
--- | ---
C-4 | —CH$_2$OR$_{13}$
C-6 | —CHO

I claim:
1. A compound of the formula

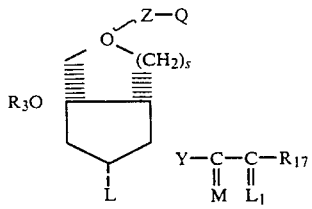

wherein D is cis $>$C=CH—, trans $>$C=CH— or $>$CHCH$_2$—;

wherein R$_3$ is hydrogen, methyl or acetyl;
wherein Z is:
(1) —CH$_2$—(CH$_2$)$_f$—C(R$_4$)$_2$— wherein each R$_4$ is the same and is hydrogen or fluoro, and f is zero, one, 2 or 3;
(2) trans-CH$_2$—CH=CH—; or
(3) —(Ph)—(CH$_2$)$_g$— wherein Ph is 1,2-, 1,3-, or 1,4-phenylene and g is zero, one, 2 or 3;
wherein Q is
(1) —COOR$_5$, wherein R$_5$ is
(a) hydrogen,
(b) (C$_1$-C$_{12}$)alkyl,
(c) (C$_3$-C$_{10}$)cycloalkyl,
(d) (C$_7$-C$_{12}$)aralkyl, (e) phenyl optionally substituted with one, 2 or 3 chloro or (C$_1$-C$_4$)alkyl,
(f) phenyl substituted in the para-position with —NHCOR$_6$, —COR$_7$, —OC(O)R$_8$ or —CH=N—NHCONH$_2$, wherein R$_6$ is methyl, phenyl, acetamidophenyl, benzamidophenyl or —NH$_2$; R$_7$ is methyl, phenyl, —NH$_2$, or methoxy; and R$_8$ is phenyl or acetamidophenyl;
(g) phthalidyl,
(h) 3-(5,5-dimethyl-1,3,2-dioxaphosphorinan-2-yl)-2-oxopropan-1-yl P-oxide,
(i) 3-(5,5-di(hydroxymethyl)-1,3,2-dioxaphosphorinan-2-yl)-2-oxopropan-1-yl P-oxide, or
(j) a pharmacologically acceptable cation;
(2) —CH$_2$OH;
(3) —COL$_2$, wherein L$_2$ is
(a) an amino group of the formula —NR$_9$R$_{10}$ wherein R$_9$ is hydrogen or (C$_1$-C$_{12}$)alkyl and R$_{10}$ is
(i) hydrogen
(ii) (C$_1$-C$_{12}$)alkyl
(iii) (C$_3$-C$_{10}$)cycloalkyl,
(iv) (C$_7$-C$_{12}$)aralkyl
(v) phenyl optionally substituted with one, 2 or 3 chloro, (C$_1$-C$_3$)alkyl, hydroxy, carboxy, (C$_2$-C$_5$)alkoxycarbonyl, or nitro,
(vi) (C$_2$-C$_5$)carboxyalkyl,
(vii) (C$_2$-C$_5$)carbamoylalkyl,
(viii) (C$_2$-C$_5$)cyanoalkyl,
(ix) (C$_3$-C$_6$)acetylalkyl,
(x) (C$_7$-C$_{12}$)benzoalkyl, optionally substituted by one, 2, or 3 chloro, (C$_1$-C$_3$)alkyl, hydroxy, (C$_1$-C$_3$)alkoxy, carboxy, (C$_2$-C$_5$)-alkoxycarbonyl, or nitro,
(xi) pyridyl, optionally substituted by one, 2, or 3 chloro, (C$_1$-C$_3$)alkyl, or (C$_1$-C$_3$)alkoxy,
(xii) (C$_6$-C$_9$)pyridylalkyl optionally substituted by one, 2, or 3 chloro, (C$_1$-C$_3$)alkyl, hydroxy, or (C$_1$-C$_3$)alkyl,
(xiii) (C$_1$-C$_4$)hydroxyalkyl,
(xiv) (C$_1$-C$_4$)dihydroxyalkyl,
(xv) (C$_1$-C$_4$)trihydroxyalkyl;
(b) cycloamine selected from the group consisting of pyrolidino, piperidino, morpholino, piperazino, hexamethyleneimino, pyrroline, or 3,4-didehydropiperidinyl optionally substituted by one or 2 (C$_1$-C$_{12}$)alkyl;
(c) carbonylamino of the formula —NR$_{11}$COR$_{10}$, wherein R$_{11}$ is hydrogen or (C$_1$-C$_4$)alkyl and R$_{10}$ is other than hydrogen, but otherwise defined as above;
(d) sulfonylamino of the formula —NR$_{11}$SO$_2$R$_{10}$, wherein R$_{11}$ and R$_{10}$ are defined in (c);
(4) —CH$_2$NL$_3$L$_4$, wherein L$_3$ and L$_4$ are hydrogen or (C$_1$-C$_4$)alkyl, being the same or different, or the pharmacologically acceptable acid addition salts thereof when Q is —CH$_2$NL$_3$L$_4$; or
(5) —CN;
wherein s is the integer one or 2;
wherein L is H,H; α-OR$_{12}$,β-H; βOR$_{12}$; α-CH$_2$OR$_{12}$,β-H; α-H,β-CH$_2$OR$_{12}$
wherein R$_{12}$ is hydrogen or a hydroxyl protecting group;
wherein Y is trans —CH=CH—, cis-CH=CH—, —CH$_2$CH$_2$—, or —C≡C—;
wherein M is α-OR$_{12}$,β-R$_{14}$; or α-R$_{14}$,β-OR$_{12}$, wherein R$_{12}$ is as defined above, and R$_{14}$ is hydrogen or methyl;

wherein L₁ is α-R₁₅,β-R₁₆; α-R₁₆,β-R₁₅; or a mixture thereof wherein R₁₅ and R₁₆ are hydrogen, methyl, or fluoro being the same or different with the proviso that one of R₁₅ and R₁₆ is fluoro only when the other of R₁₅ and R₁₆ is hydrogen or fluoro;

wherein R₁₇ is (1) —C$_m$H$_{2m}$CH₃ wherein m is an integer of from one to 5, (2) phenoxy optionally substituted by one, 2, or 3 chloro, fluoro, trifluoromethyl, (C₁-C₃)alkyl, or (C₁-C₃)alkoxy, with the proviso that not more than two substituents are other than alkyl and with the proviso that R₁₇ is phenoxy or substituted phenoxy, only when R₁₅ and R₁₆ are hydrogen or methyl, being the same or different;

(3) phenyl, benzyl, phenylethyl, or phenylpropyl optionally substituted on the aromatic ring by one, 2, or 3 chloro, fluoro, trifluoromethyl (C₁-C₃)alkyl, or (C₁-C₃)alkoxy, with the proviso that not more than two substituents are other than alkyl, (4) cis-CH=CH—CH₂CH₃,
(5) —(CH₂)₂—CH(OH)—CH₃,
(6) —(CH₂)₃—CH=C(CH₃)₂,
(7)

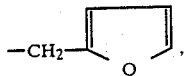

or
(8)

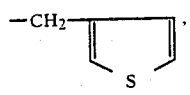

or wherein

taken together is
(1) (C₄-C₇)cycloalkyl optionally substituted by one to 3 (C₁-C₅)-alkyl,
(2) 3-thienyloxymethyl,
(3)

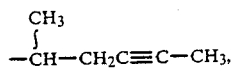

(4) —C≡C—C$_q$H$_{2q}$CH₃ wherein q is an integer of from 2 to 6, or
(5) —C$_p$H$_{2p}$CH=CH₂ wherein p is an integer of from 3 to 7; and individual optical isomers thereof.

2. A compound of claim 1 wherein R₁₂ is hydrogen or a pharmacologically acceptable salt thereof.

3. A compound of claim 2 wherein s is one and D is cis >C=CH— or trans >C=CH—.

4. A compound of claim 3 wherein Y is trans-CH=CH—, —C≡C— or —CH₂CH₂—.

5. A compound of claim 4 wherein Q is —COOR₅ or COL₂ wherein L₂ is an amine group of the formula —NR₉R₁₀.

6. A compound of claim 5 wherein R₁₇ is —C$_m$H$_{2m}$CH₃ wherein m is an integer of from one to 5; phenoxy; phenyl; benzyl; or 3-thienylmethyl; or wherein

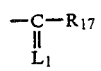

taken together is cyclohexyl; 3-ethylcyclobutyl; 3-thienyloxymethyl; or

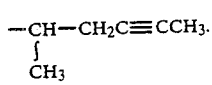

7. A compound of claim 6 wherein R₅ is hydrogen, a pharmacologically acceptable cation, methyl or ethyl, and R₁₇ is —C$_m$H$_{2m}$CH₃ wherein m is an integer of from one to 5 carbon atoms or wherein

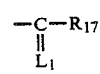

taken together is

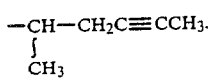

8. A compound of claim 7 which is the 5Z isomer.
9. A compound of claim 8 which is 5(E or Z)-2-decarboxy-2-methyloxy-9β-hydroxy-6a-carba-prostaglandin I₂.
10. A compound of claim 7 which is (5Z)-9β-hydroxy-6a-carba-prostaglandin I₂.
11. A compound of claim 7 which is (5Z)-9β-methoxy-6a-carba-prostaglandin I₂.
12. A compound of claim 7 which is (5Z)-9β-acetoxy-6a-carba-prostaglandin I₂.
13. A compound of the formula

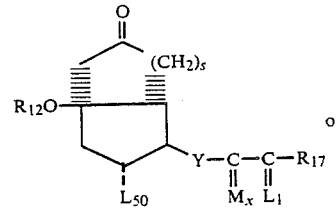 or

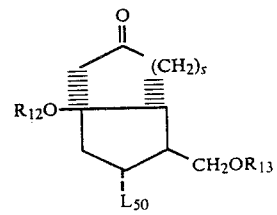

wherein s is the integer one or 2;

wherein $R_{12}$ is hydrogen or a protecting group;

wherein $L_{50}$ is H,H; α-OR,β-H; α-H,β-OR; α-CH$_2$OR,β-H; α-H,β-CH$_2$OR wherein R is a hydroxyl protecting group;

wherein Y is trans —CH=CH—, cis-CH=CH—, —CH$_2$CH$_2$—, or —C≡C—;

wherein $M_x$ is α-OR,β-$R_{14}$; or α-$R_{14}$,β-OR, wherein R is as defined above, and $R_{14}$ is hydrogen or methyl;

wherein R is a hydroxyl protecting group;

wherein $L_1$ is α-$R_{15}$,β-$R_{16}$; α-$R_{16}$,β-$R_{15}$; or a mixture thereof wherein $R_{15}$ and $R_{16}$ are hydrogen, methyl, or fluoro being the same or different with the proviso that one of $R_{15}$ and $R_{16}$ is fluoro only when the other of $R_{15}$ and $R_{16}$ is hydrogen or fluoro;

wherein $R_{17}$ is (1) —C$_m$H$_{2m}$CH$_3$ wherein m is an integer of from one to 5, (2) phenoxy optionally substituted by one, 2, or 3 chloro, fluoro, trifluoromethyl, (C$_1$-C$_3$)alkyl, or (C$_1$-C$_3$)alkoxy, with the proviso that not more than two substituents are other than alkyl and with the proviso that $R_{17}$ is phenoxy or substituted phenoxy, only when $R_{15}$ and $R_{16}$ are hydrogen or methyl, being the same or different;

(3) phenyl, benzyl, phenylethyl, or phenylpropyl optionally substituted on the aromatic ring by one, 2, or 3 chloro, fluoro, trifluoromethyl (C$_1$-C$_3$)alkyl, or (C$_1$-C$_3$)alkoxy, with the proviso that not more than two substituents are other than alkyl, (4) cis-CH=CH—CH$_2$CH$_3$, (5) —(CH$_2$)$_2$—CH(OH)—CH$_3$, (6) —(CH$_2$)$_3$—CH=C(CH$_3$)$_2$, (7)

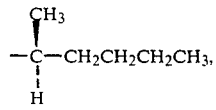

(8)

(9)

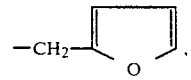

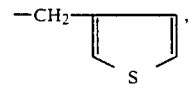

or wherein

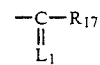

taken together is (1) (C$_4$-C$_7$)cycloalkyl optionally substituted by one to 3 (C$_1$-C$_5$)-alkyl, (2) 3-thienyloxymethyl, (3)

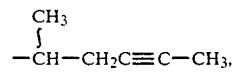

(4)

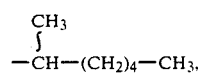

(5) —C≡C—C$_q$H$_{2q}$CH$_3$ wherein q is an integer of from 2 to 6, or (6) —C$_p$H$_{2p}$CH=CH$_2$ wherein p is an integer of from 3 to 7; and individual isomers thereof.

* * * * *